US011275065B2

(12) United States Patent
Kobold et al.

(10) Patent No.: US 11,275,065 B2
(45) Date of Patent: Mar. 15, 2022

(54) AUTOMATED CLINICAL DIAGNOSTIC SYSTEM AND METHOD

(71) Applicant: Roche Diagnostics Operations, Inc., Indianapolis, IN (US)

(72) Inventors: Uwe Kobold, Weilhelm (DE); Hubert Paul, Wielenbach (DE); Martin Rempt, Penzberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 293 days.

(21) Appl. No.: 16/718,296

(22) Filed: Dec. 18, 2019

(65) Prior Publication Data

US 2020/0124576 A1   Apr. 23, 2020

Related U.S. Application Data

(63) Continuation of application No. PCT/EP2018/067739, filed on Jul. 2, 2018.

(30) Foreign Application Priority Data

Jul. 4, 2017 (EP) .................................. 17179534

(51) Int. Cl.
*G01N 30/72* (2006.01)
*G01N 30/86* (2006.01)
(Continued)

(52) U.S. Cl.
CPC ..... *G01N 30/7233* (2013.01); *G01N 30/8631* (2013.01); *G01N 30/8665* (2013.01);
(Continued)

(58) Field of Classification Search
CPC .......... G01N 30/7233; G01N 30/8631; G01N 30/8665; G01N 30/88; G01N 33/487;
(Continued)

(56) References Cited

U.S. PATENT DOCUMENTS 10,775,355 B2 * 9/2020 Franz .................. G01N 30/466
2008/0312893 A1 * 12/2008 Denton ................. G16H 10/40
703/11
(Continued)

FOREIGN PATENT DOCUMENTS

JP    2016-170079 A    9/2016
WO   2003/065406 A1   8/2003
(Continued)

OTHER PUBLICATIONS

International Search Report dated Aug. 3, 2018, in Application No. PCT/2018/067739, 2 pp.

*Primary Examiner* — David A Vanore
(74) *Attorney, Agent, or Firm* — Roche Diagnostics Operations, Inc.

(57) ABSTRACT

A diagnostic system and method and an interconnected laboratory system comprising clinical diagnostic systems are presented. The diagnostic system comprises a sample preparation module, a liquid chromatography (LC) separation module coupled to the sample preparation module via a sample preparation/LC interface, a mass spectrometer (MS) module coupled to the LC separation module via an LC/MS interface, and a result calculation module for identifying and/or quantifying analytes or substances of interest contained in the samples and passed through the LC separation and MS modules. The diagnostic system comprises a controller programmed to monitor operational parameters (1-$n$) indicative of a performance status of the diagnostic system, to trigger a quality control procedure and/or a maintenance procedure whenever one or more parameters (1-$n$) of the operational parameters (1-$n$) is out of specification, and to minimize the quality control and/or maintenance procedures as long as the operational parameters (1-$n$) remains within specification.

15 Claims, 12 Drawing Sheets

(51) Int. Cl.
*G01N 30/88* (2006.01)
*G01N 33/487* (2006.01)
*G01N 30/02* (2006.01)

(52) U.S. Cl.
CPC ........... *G01N 30/88* (2013.01); *G01N 33/487* (2013.01); *G01N 2030/027* (2013.01); *G01N 2030/8813* (2013.01)

(58) Field of Classification Search
CPC ..... G01N 2030/027; G01N 2030/8813; G01N 35/0092; G01N 2030/8804; G01N 35/00594; G01N 35/00584; G01N 30/72; G01N 1/405
See application file for complete search history.

(56) References Cited

U.S. PATENT DOCUMENTS

| | | | |
|---|---|---|---|
| 2014/0033793 A1* | 2/2014 | Thorson | G01N 30/8665 73/1.02 |
| 2014/0073043 A1* | 3/2014 | Holmes | G01N 33/5005 435/287.3 |
| 2014/0296089 A1* | 10/2014 | Holmes | B01L 9/06 506/9 |
| 2016/0054343 A1* | 2/2016 | Holmes | G01N 21/75 506/2 |
| 2018/0292368 A1* | 10/2018 | Franz | G01N 30/24 |
| 2020/0124576 A1* | 4/2020 | Kobold | G01N 1/405 |
| 2021/0190736 A1* | 6/2021 | Geiger | G01N 30/7233 |

FOREIGN PATENT DOCUMENTS

| | | |
|---|---|---|
| WO | 2005/098463 A2 | 10/2005 |
| WO | 2008/146440 A1 | 12/2008 |
| WO | 2012/058632 A1 | 5/2012 |
| WO | 2017/103180 A1 | 6/2017 |

* cited by examiner

| Sample Number | Retention Time Analyte of interest [min] ((Spec: 4.5min-7.2min)) | Mass Resolution [FWHM] ((Spec: 8200-8600)) | Absolute Intensity [cps] (( Spec: 10-1500)) | Accurate Mass error [ppm] ((Spec: -10 - +10)) | Observation | Action |
|---|---|---|---|---|---|---|
| 1 | 5.48 | 8315 | 524 | -1 | OK | None |
| 2 | 5.53 | 8428 | 436 | -7 | OK | None |
| 3 | 5.49 | 8537 | 883 | -16 | Bad Mass accuracy | Recalibration |
| 4 | 5.53 | 8441 | 1240 | -1 | OK | None |
| 5 | 5.48 | 8443 | 710 | 25 | Bad Accurate mass; Lock mass for mass correction out of volume | Refill of lock mass substance; Cleaning of source |
| 6 | 5.53 | 8306 | 577 | 39 | Bad Accurate mass; Annual Maintenance and insufficient calibration | Recalibration |
| 7 | 7.9 | 8315 | 673 | -2 | Out of spec for the retention time; insufficient degasser flushing from FA to TFA System | Replace eluent and flush |
| 8 | 7.12 | 8303 | 378 | -2 | OK | None |
| 9 | 6.99 | 8403 | 364 | -5 | OK | None |
| 10 | 6.47 | 8441 | 713 | 2 | OK | None |
| 11 | 6.44 | 8154 | 639 | -30 | Low Resolution and bad accurate mass | Tuning of the MS module |
| 12 | 7.5 | 8571 | 3380 | -2 | Out of spec for the retention time; wrong eluent system installed | Replace eluent and flush |
| 13 | 6.57 | 8327 | 270 | -2 | OK | None |
| 14 | 6.15 | 8352 | 535 | -3 | OK | None |
| 15 | 6.32 | 8390 | 2160 | 0 | OK | None |
| 16 | 6.08 | 8289 | 1410 | -9 | OK | None |
| 17 | 5.99 | 8390 | 1130 | 0 | OK | None |
| 18 | 5.96 | 8530 | 1150 | -17 | OK | None |
| 19 | 5.77 | 8253 | 211 | 0 | OK | None |
| 20 | 5.77 | 8205 | 336 | 2 | Bad Mass accuracy | Recalibration |
| 21 | 5.73 | 8241 | 247 | 0 | OK | None |
| 22 | 5.74 | 8774 | 197 | -2 | OK | None |
| 23 | 6.15 | 8558 | 140 | 2 | OK | None |
| 24 | 5.96 | 8545 | 5000 | -2 | OK | None |
| 25 | 5.66 | 8441 | 230 | 0 | OK | None |
| 26 | 5.82 | 8315 | 186 | 0 | OK | None |
| 27 | 5.77 | 8365 | 150 | -3 | OK | None |

AUTOMATED CLINICAL DIAGNOSTIC SYSTEM AND METHOD

CROSS-REFERENCE TO RELATED APPLICATIONS

This application is a continuation of PCT/EP2018/067739, filed Jul. 2, 2018, which is based on and claims priority to EP 17179534.7, filed Jul. 4, 2017, which are hereby incorporated by reference.

BACKGROUND

The present disclosure generally relates to a clinical diagnostic system and method that includes automated sample preparation, liquid chromatography and mass spectrometry as well as an interconnected laboratory system comprising a plurality of clinical diagnostic systems.

There is growing interest for the implementation of mass spectrometry and more specifically of liquid chromatography coupled to mass spectrometry in the clinical laboratory.

The use of mass spectrometry, however, may face regulatory challenges to be approved for clinical diagnostics. This is mostly because of lack of standardized procedures, except for a very few analytes, and because of the still large number of user dependent factors, e.g., due to a number of manual steps that are still conducted and the diversity of hardware components that may be used and combined and that play a role in delivering reliable and reproducible results of clinical relevance. In particular, sample preparation is typically a manual and tedious procedure. Protein precipitation with subsequent centrifugation is the most popular method to remove unwanted and potentially disturbing sample matrix. The use of kits may in part facilitate sample preparation that can be, at least in part, automated. Kits are however available only for a limited number of analytes of interest and the entire process from sample preparation, to separation and detection remains complex, requiring the attendance of highly trained laboratory personnel to run highly sophisticated instruments.

Also, typically, a batch approach is followed where a batch of samples prepared in advance under the same preparation conditions undergo consecutive separation runs under the same separation conditions. This approach however does not enable high throughput and is not flexible, e.g., does not allow re-scheduling (changing a pre-defined processing sequence) in view, for example, of incoming emergency samples that have higher priority and have to be processed first.

A system and an automated workflow that make use of LC coupled to mass spectrometry more convenient, easier to use and more reliable and therefore suitable for clinical diagnostics is disclosed e.g., in WO2017103180A1. In particular, high throughput, e.g., up to 100 samples/hour or more with random access sample preparation can be in principle obtained.

Despite automation, however, the effective throughput and usability of such a technically complex system and associated workflow, may be affected by the fact that a significant part of the operational time may have to be dedicated to the execution of quality control procedures such as e.g., referred to in the recent CLSI C62-A guideline, in order to make sure that, after an initial system suitability check, the system continues to operate according to specification. Whereas this practice may be acceptable for a batch-mode approach where e.g., only one analyte of interest at a time for several samples is measured and the same reagent or reagents are used, it becomes much more inefficient for a random access approach where processing of different samples and testing for different analytes may occur in a random sequence and where different reagents for preparing samples according to the type of sample and/or to the analytes of interest are used, meaning that a different quality control procedure for each different analyte/reagent and each sample/analyte specific workflow may be required.

Furthermore, after successful passing a quality control procedure, if any component of the system, e.g., any of the several components of the sample preparation module, of the liquid chromatography module, of the MS module, has a technical malfunction or failure, such a malfunction or failure can be often detected only when executing the next scheduled quality control procedure. As a consequence, all results obtained in between two quality control procedures may have to be flagged and/or rejected and the samples may have to be processed once again after successful elimination of the root cause and passing again the quality control procedure. For some samples, there might be not sufficient sample volume left to repeat the measurement, e.g., for sample from a newborn, or may be difficult or complicated and time consuming to return to an input position for repeating the entire process. Thus, a higher frequency of quality control procedures may be important in order to more frequently check the operational status of the system, while compromising sample processing throughput even further.

Therefore, there is a need for a clinical diagnostic system and method that are capable of ensuring analytical performance of the system without unnecessarily compromising sample processing throughput as well as identifying eventual malfunctions and failures in real time as they occur and, in some cases, even predicting them before they occur.

SUMMARY

According to the present disclosure, a clinical diagnostic system is presented. The clinical diagnostic system can comprise a sample preparation module for the automated preparation of samples, a liquid chromatography (LC) separation module coupled to the sample preparation module via a sample preparation/LC interface, a mass spectrometer (MS) module coupled to the LC separation module via an LC/MS interface, a result calculation module for identifying and/or quantifying analytes or substances of interest contained in the samples and passed through the LC separation module and the MS module, and a controller programmed to monitor a predetermined set of operational parameters ($1$-$n$) indicative of a performance status of the clinical diagnostic system, trigger a quality control procedure and/or a maintenance procedure whenever one or more parameters ($1$-$n$) of the predetermined set of operational parameters ($1$-$n$) is out of specification, and minimize the quality control and/or maintenance procedures as long as the set of operational parameters ($1$-$n$) remains within specification.

Accordingly, it is a feature of the embodiments of the present disclosure to provide for a clinical diagnostic system and method that are capable of ensuring analytical performance of the system without unnecessarily compromising sample processing throughput as well as identifying eventual malfunctions and failures in real time as they occur and, in some cases, even predicting them before they occur. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which:

FIG. 4 illustrates a table with examples of operational parameters according to an embodiment of the present disclosure.

FIG. 10 illustrates schematically examples of operational parameters of the MS module according to an embodiment of the present disclosure.

FIG. 11 illustrates schematically other examples of operational parameters of the MS module according to an embodiment of the present disclosure.

FIG. 12 illustrates schematically other examples of operational parameters of the MS module according to an embodiment of the present disclosure.

FIG. 13 illustrates schematically other examples of operational parameters of the MS module according to an embodiment of the present disclosure.

DETAILED DESCRIPTION

Figure 1:
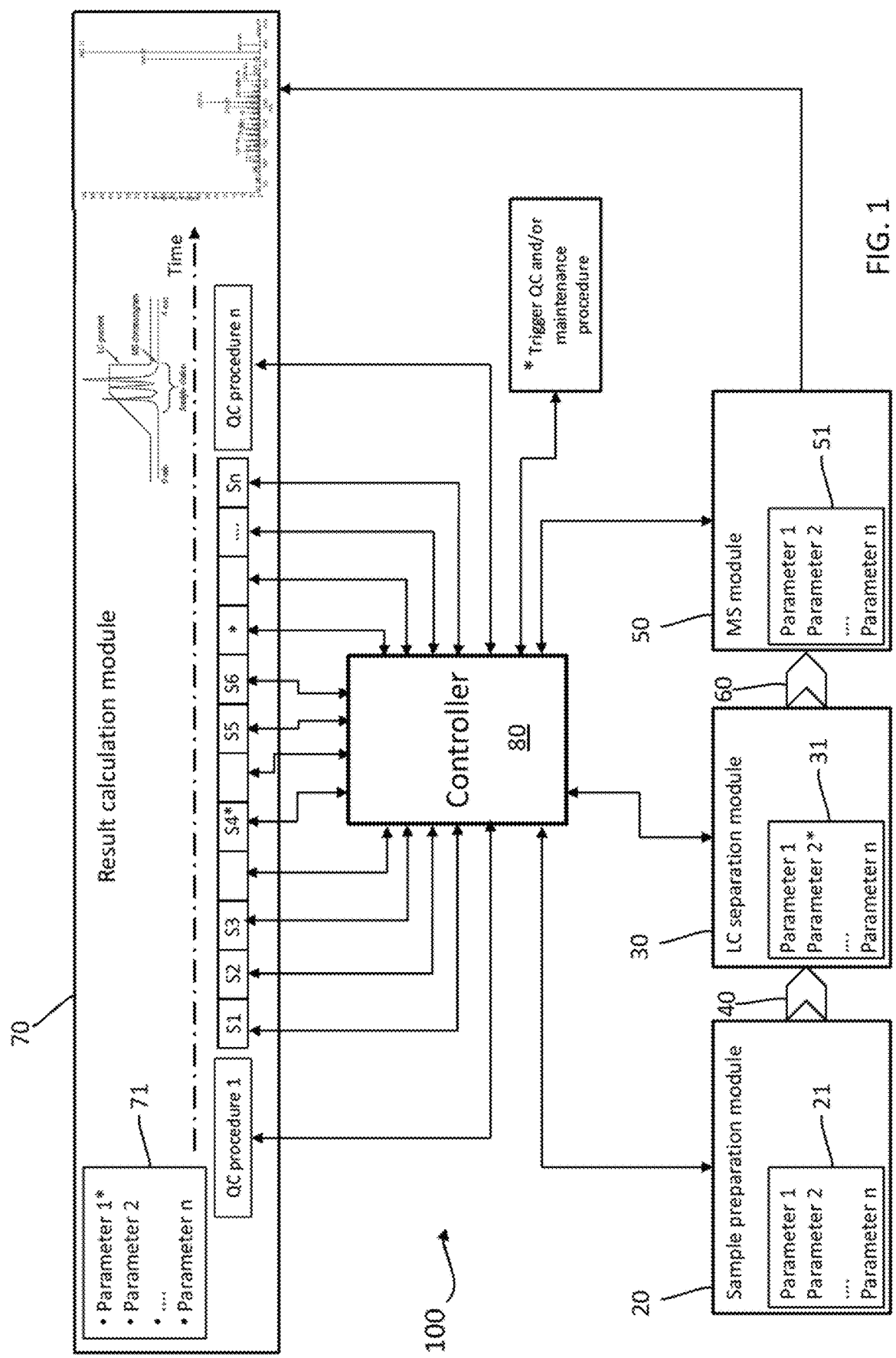
FIG. 1 illustrates schematically an example of clinical diagnostic system according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A clinical diagnostic system and a clinical diagnostic method are herein introduced, that are capable of ensuring analytical performance of the system without unnecessarily compromising sample processing throughput. Another advantage is that eventual malfunctions and failures can be identified in real time as they occur and in some cases even predicted before they occur, thereby triggering corrective measures before eventually additional samples are processed. An interconnected laboratory system comprising a plurality of clinical diagnostic systems is also introduced.

The clinical diagnostic system can comprise a sample preparation module for the automated preparation of samples, a liquid chromatography (LC) separation module coupled to the sample preparation module via a sample preparation/LC interface, a mass spectrometer (MS) module coupled to the LC separation module via an LC/MS interface, and a result calculation module for identifying and/or quantifying analytes or substances of interest contained in the samples and passed through the LC separation module and the MS module.

The clinical diagnostic system can further comprise a controller. The controller can be programmed to monitor a predetermined set of operational parameters indicative of a performance status of the clinical diagnostic system. The controller can further be programmed to trigger a quality control procedure and/or a maintenance procedure whenever one or more parameters of the predetermined set of operational parameters is out of specification and to minimize the quality control and/or maintenance procedures as long as the set of operational parameters remains within specification.

A "clinical diagnostics system" can be a laboratory automated apparatus dedicated to the analysis of samples for in vitro diagnostics. The clinical diagnostics system may have different configurations according to the need and/or according to the desired laboratory workflow. Additional configurations may be obtained by coupling a plurality of apparatuses and/or modules together. A "module" can be a work cell, typically smaller in size than the entire clinical diagnostics system, which can have a dedicated function. This function can be analytical but can be also pre-analytical or post analytical or it can be an auxiliary function to any of the pre-analytical function, analytical function or post-analytical function. In particular, a module can be configured to cooperate with one or more other modules for carrying out dedicated tasks of a sample processing workflow, e.g., by performing one or more pre-analytical and/or analytical and/or post-analytical steps. Thus, the clinical diagnostic system may comprise one analytical apparatus or a combination of any of such analytical apparatuses with respective workflows, where pre-analytical and/or post analytical modules may be coupled to individual analytical apparatuses or be shared by a plurality of analytical apparatuses. In the alternative, pre-analytical and/or post-analytical functions may be performed by units integrated in an analytical apparatus. The clinical diagnostics system can comprise functional units such as liquid handling units for pipetting and/or pumping and/or mixing of samples and/or reagents and/or system fluids and also functional units for sorting, storing, transporting, identifying, separating, detecting. In particular, the clinical diagnostics system can comprise a sample preparation module, a liquid chromatography separation module, a mass spectrometry module, and a result calculation module, either distinguishable as individual and exchangeable units coupled to each other or at least in part integrated into a common system housing.

The term "sample" can herein be generally used to indicate either a test sample or a QC sample or a calibrator.

The term "test sample" can refer to a biological material suspected of containing one or more analytes of interest and whose detection, qualitative and/or quantitative, may be associated to a clinical condition. The test sample can be derived from any biological source, such as a physiological fluid, including blood, saliva, ocular lens fluid, cerebral spinal fluid, sweat, urine, milk, ascites fluid, mucous, synovial fluid, peritoneal fluid, amniotic fluid, tissue, cells or the like. The test sample can be pretreated prior to use, such as preparing plasma from blood, diluting viscous fluids, lysis or the like; methods of treatment can involve filtration, centrifugation, distillation, concentration, inactivation of interfering components, and the addition of reagents. A test sample may be used directly as obtained from the source in some cases or following a pretreatment and/or sample preparation workflow to modify the character of the sample, e.g., after adding an internal standard, after being diluted with another solution or after having being mixed with reagents e.g., to enable carrying out one or more in vitro diagnostic tests, or for enriching (extracting/separating/concentrating) analytes of interest and/or for removing matrix components potentially interfering with the detection of the analyte(s) of interest. Examples of analytes of interest are vitamin D, drugs of abuse, therapeutic drugs, hormones, and metabolites in general. The list is however not exhaustive.

The term "QC sample" can refer to a reference sample that mimics a test sample and that contains known values of one or more QC substances. Typically, QC samples can be supplied in one or more levels, e.g., two or three or more levels, that correspond to different concentration ranges of the QC substances. QC samples can typically be measured in the same way and under the same conditions as test samples are measured in order to check that a calibrated system is actually within the specifications or admissible range.

A "QC substance" can be an analyte identical to an analyte of interest, the concentration of which is known, or that generates by reaction or derivatization, e.g., by fragmentation, an analyte identical to an analyte of interest, the concentration of which is known, or it can be any other equivalent substance of known concentration which mimics the analyte of interest or that can be otherwise correlated to a certain analyte of interest, e.g., a substance having similar log P value and/or mass to that of an analyte of interest or an isotopic substance.

A "calibrator" can be a calibration solution that contains known values of one or more calibration materials used for calibration and that can be measured under the same conditions as a test or QC sample. Typically, one or two calibrators can be used for a one-point or two-point calibration respectively, in the case of linear response to analyte concentrations. Three or more calibrators may be used if the calibration curve is non-linear. In particular, also calibrators can be provided in different levels that correspond to different concentration ranges of the calibration materials.

A calibration material can be the same as a QC substance.

A "sample preparation module" can be a pre-analytical module coupled to an analytical apparatus or module designed to execute a series of sample processing steps aimed at removing or at least reducing interfering matrix components in a sample and/or enriching analytes of interest in a sample. Such processing steps may include any one or more of the following processing operations carried out on a sample or a plurality of samples, sequentially, in parallel or in a staggered manner: pipetting (aspirating and/or dispensing) fluids, pumping fluids, mixing with reagents, incubating at a certain temperature, heating or cooling, centrifuging, separating, filtering, sieving, drying, washing, resuspending, aliquoting, transferring, storing, and the like.

According to an embodiment, the sample preparation module can comprise a magnetic bead handling unit for treating samples with reagents comprising magnetic beads carrying analyte and/or matrix selective groups for extracting/enriching analytes of interest and removing or at least reducing matrix components. In particular, the magnetic bead handling unit can comprise at least one magnetic or electromagnetic workstation for holding at least one reaction container and for manipulating magnetic beads added to a sample or samples contained therein. The magnetic bead handling unit may further comprise a mixing mechanism for mixing fluids and/or resuspending the magnetic beads in the reaction container(s), e.g., by shacking or agitating the reaction container(s), e.g., by an eccentric rotation mechanism. Alternatively, the bead handling unit may be a flow-through system where the magnetic beads are captured in a channel or capillary flow-through device. According to this embodiment, capturing, washing and releasing of analytes can be done by repeatedly magnetically capturing and releasing beads in a flow-through channel.

The term "bead" may not necessarily refer to a spherical shape but to a particle having an average size in the nanometer or micrometer range and having any possible shape.

Non-magnetic beads may also be used. In that case, capturing and releasing may be based on filtration or centrifugation for example. The sample preparation module may further comprise one or more pipetting device or fluid transport device for adding/removing fluids such as samples, reagents, wash fluids, suspension fluids, into/from the reaction container(s).

The sample preparation module may further comprise a reaction container transporting mechanism.

In the alternative, or in addition, to magnetic bead handling, other techniques may be used such as protein precipitation followed by centrifugation, cartridge based solid phase extraction, pipette tip based solid phase extraction, liquid liquid extraction, affinity based extraction (immunosorption, molecular imprints, aptamers, and the like).

A "reagent" can be a substance used for treatment of a sample in order e.g., to prepare a sample for analysis, to enable a reaction to occur, or to enable detection of a physical parameter of the sample or analyte contained in the sample. In particular, a reagent can be a substance that is or comprises a reactant, typically a compound or agent capable e.g., of binding to or chemically transforming one or more analytes present in a sample or an unwanted matrix component of the sample. Examples of reactants are enzymes, enzyme substrates, conjugated dyes, protein-binding molecules, ligands, nucleic acid binding molecules, antibodies, chelating agents, promoters, inhibitors, epitopes, antigens, and the like. However, the term reagent can be used to include any fluid that can be added to a sample including a dilution liquid, including water or other solvent or a buffer solution, or a substance that can be used for disruption of specific or nonspecific binding of an analyte to a protein, binding proteins or surfaces.

Sample may be provided, for example, in sample containers such as sample tubes, including primary tubes and secondary tubes, or multi-well plates, or any other sample carrying support. Reagents may be arranged, for example, in the form of containers or cassettes containing individual reagents or group of reagents and placed in appropriate receptacles or positions within a storage compartment or conveyor. Other types of reagents or system fluids may be provided in bulk containers or via a line supply.

The term "test fluid" can be used to indicate either a sample or a reagent or a mixture of a sample and a reagent, unless specified.

A "liquid chromatography (LC) separation module" can be an analytical module designed to subject the prepared samples to chromatographic separation in order, for example, to separate analytes of interest from matrix components, e.g., remaining matrix components after sample preparation that may still interfere with a subsequent detection and/or in order to separate analytes of interest from each other in order to enable their individual detection. According to an embodiment, the LC separation module can be an intermediate analytical module designed to prepare a sample for mass spectrometry and/or to transfer the prepared sample to a mass spectrometer. In particular, typically, during an LC run, the mass spectrometer may be set to scan a specific mass range. LC/MS data can be represented by adding up the ion current in the individual mass scans and plotting that "totaled" ion current as an intensity point against time. The resulting plot looks like an HPLC UV trace with analyte peaks. The LC separation module may otherwise comprise a detector of its own such as a UV detector.

The LC separation module may be embodied as a multi-channel LC module comprising a plurality of LC channels arranged in parallel.

An "LC channel" can be a fluidic line comprising at least one capillary tubing and/or LC column comprising a stationary phase selected according to the type of sample(s) and analytes and through which a mobile phase can be pumped in order to trap and/or separate and elute and/or transfer analytes of interest under selected conditions, e.g., according to their polarity or log P value, size or affinity, as generally known. The at least one LC column in the at least one LC channel may be exchangeable. In particular, the LC separation module may comprise more LC columns than LC channels where a plurality of LC columns may be interchangeably coupled to the same LC channel. A capillary tubing may bypass an LC column or may allow adjustment of dead volumes to fine-tune elution time windows.

According to certain embodiments, the LC separation module can comprise at least one faster LC channel with a shorter cycle time and at least one slower LC channel with a longer cycle time. However, the LC separation module may alternatively comprise at least two faster LC channels without slower LC channels or at least two slower LC channels without faster LC channels.

A "cycle time" can be the time that it takes from a sample input (injection) into an LC channel until the same LC channel is ready for another sample input. In other words, a cycle time can be the minimum time elapsing between two consecutive sample inputs in the same LC channel under pre-determined conditions and can be measured in seconds. The cycle time can include injection time, separation time until elution of the last analyte of interest, and re-equilibration time in order to prepare the column for a new injection.

The terms "faster" and "slower" with reference to an LC channel can only be relative terms used to compare different LC channels between them in the same LC separation module. In particular, the terms can be related to the duration of the cycle time and not necessarily to the resolution capabilities of the LC channels. However, typically, a slower LC channel can have a higher resolution than a faster LC channel and a faster LC channel can have a lower resolution than a slower LC channel where in the faster LC channel resolution may be compromised in favor of speed. Typically, a faster LC channel can have a cycle time of less than 60 seconds, e.g., from about 5 seconds up to about 60 seconds, more typically in the range of 20-40 seconds, whereas a slower LC channel can have a cycle time of more than 60 seconds, typically can have a cycle time in the range between about 60 seconds and about 600 seconds, more typically 60-400 seconds.

According to an embodiment, the LC separation module can comprise at least two faster LC channels or at least one faster LC channel with at least two interchangeable LC columns and at least two slower LC channels, e.g., two faster LC channels and four slower LC channels. The slower LC channels may be the same or different between them, e.g., one comprising a HILIC column and one comprising a reversed phase (RP) or a pentafluorophenyl (PFP) column where the conditions can be selected such that the cycle time can be the same for different columns respectively. The faster LC channel(s) may be the same or different between them respectively, e.g., one comprising a HILIC column and one comprising a reversed phase (RP) or a pentafluorophenyl (PFP) column where the conditions can be selected such that the cycle time can be the same for different columns respectively.

According to an embodiment, the at least one faster LC channel can be a capillary flow injection analysis (FIA) channel or a rapid trap and elute online liquid chromatography channel and the at least one slower LC channel can be an ultra-high-performance liquid chromatography (UHPLC) channel.

In particular, depending on the analytes of interest each prepared sample may be inputted into a faster LC channel or into a slower LC channel. For example, if a sample requires only analyte purification and concentration, since sufficient separation can be obtained, for example, in a subsequent mass spectrometry analysis and/or other separation technique, the sample can be inputted into a faster LC channel, e.g., a FIA or rapid trap and elute online liquid chromatography channel. In such a case, a stationary phase is chosen that can retain the analytes of interest whereas any salts, buffer, detergents and other matrix components are unretained and washed away. This process can typically be followed by elution of the analytes, e.g., in back flush mode, with a different mobile phase or a solvent gradient. Depending on the analytes, separation of some analytes may be expected in some cases. On the other hand, in the case of analytes having identical masses (isobaric) and/or overlapping daughter ion spectra in multiple reaction monitoring (MRM), when it comes to mass spectrometry, a more extensive chromatographic separation might be preferable. In that case, the sample can be imputed into a slower LC channel, e.g., a UHPLC channel.

The LC separation module can typically further comprise a sufficient number of pumps, e.g., binary pumps in case of conditions requiring the use of elution gradients, and several switching valves.

A "sample preparation/LC interface" can either be a module between the sample preparation module and the LC separation module or a unit integrated in the sample preparation module or in the LC separation module or sharing components between the sample preparation module and the LC separation module. The sample preparation/LC interface may comprise a container handling unit or a prepared sample receiving unit with any one or more of a holding function, a gripping function, a transfer function. According to an embodiment, the prepared sample receiving unit can be a reusable recess into which prepared samples can be received one after another according to the prepared sample output sequence just before being inputted into an LC channel, where the recess may be washed between consecutive samples.

The sample preparation/LC interface can comprise a liquid handling unit to input prepared samples to any of the LC channels. The liquid handling unit may comprise any one or more of a pipetting device, a pump, an autosampler, a flow-injection device, one or more switching valves, in particular, at least one switching valve to switch between LC channels. In particular, the container handling unit and the liquid handling unit can be designed to enable random access of any available LC channel to any prepared sample.

A "mass spectrometer (MS) module" can be an analytical module comprising a mass spectrometer and, in particular, a mass analyzer designed to further separate and/or detect analytes eluted from the LC separation module based on their mass to charge ratio. According to an embodiment, the mass spectrometer can be a fast scanning mass spectrometer. According to an embodiment, the mass spectrometer can be a tandem mass spectrometer capable of selecting parent molecular ions, generating fragments by collision induced fragmentation and separating the fragments or daughter ions according to their mass to charge (m/z) ratio. According to an embodiment, the mass spectrometer can be a triple quadrupole mass spectrometer, as known in the art. Besides quadrupoles, other types of mass analyzers may be used as well, including time of flight, ion trap or combinations thereof.

The MS module can further comprise an LC/MS interface for coupling the LC separation module to the mass spectrometer.

According to an embodiment, the LC/MS interface can comprise an ionization source, for the generation of charged analyte molecules (molecular ions) and transfer of the charged analyte molecules into the gas phase. According to certain embodiments, the ionization source can be an electro-spray-ionization (ESI) source or a heated-electrospray-ionization (HESI) source or an atmospheric-pressure-chemical-ionization (APCI) source or an atmospheric-pressure-photo-ionization (APPI) or an atmospheric-pressure-laser-ionization (APLI) source. The LC/MS interface may comprise however a double ionization source, e.g., both an ESI and an APCI source or a modular exchangeable ionization source.

Such ionization sources are known in the art and not further elucidated here.

In order to optimize ionization conditions, it may be preferable to adjust solvent composition by adding a make-up flow directly before the ionization source to adjust pH, salts, buffers or organic content.

According to an embodiment, the LC channels can be alternately connectable to the ionization via valve switching.

According to an embodiment, the LC/MS interface can further comprise an ion mobility module between the ionization source and the mass spectrometer. According to an embodiment, the ion mobility module can be a high-field asymmetric waveform ion mobility spectrometry (FAIMS) module, as also known in the art, and that can achieve separation of molecular ions in the gas phase, including isobaric ions, in milliseconds. An ion mobility gas-phase separation before mass spectrometry can compensate for insufficient chromatographic separation, e.g., of isobaric interferences, especially for LC eluates from the at least one faster LC channel. Furthermore, ion mobility interfaces for mass spectrometers can reduce the overall background signal by preventing background and other non-specific ions to enter the mass spectrometer.

A "result calculation module" can be a computing module comprising a memory and a processor running a computer-readable program or software designed for reading and/or storing analytical data generated during sample processing and for elaborating such data in order to obtain an analytical result. An "analytical result" can be a calculation result based on measured analytical data that aims at the identification and/or quantification of one or more analytes or substances of interest contained in a sample that is passed through the LC separation module and the MS module. Elaboration of analytical data or result calculation may include discrimination of background signal from signal associated to analytes and/or substances of interest, e.g., identification of peaks and association of peaks to identity and eventually quantity of analytes and/or substances of interest. In particular, this may include analyzing the shape of LC and/or MS peaks, e.g., peak symmetry, peak width at half maximum, peak areas and borders, elution/retention time, m/z value of peak maximum, ratio of adjacent peak heights, and the like. It may also include calculating the signal/noise ratio, the background signal intensity, the slope of background signal line and the like.

The term "controller" as used herein can encompass any physical or virtual processing device and, in particular, a programmable logic controller running a computer-readable program provided with instructions to perform operations in accordance with an operation plan and, in particular, associated with monitoring a predetermined set of operational parameters indicative of the performance status of the clinical diagnostic system and with the management of quality control procedures and/or maintenance procedures based on such monitoring. The controller may be part of the result calculation module or be a separate logic entity in communication with the result calculation module. In some embodiments, the controller may be integral with a data management unit, may be comprised by a server computer and/or be part of one clinical diagnostic system or even distributed across a plurality of clinical diagnostic systems.

The controller may be also configurable to control the clinical diagnostic system in a way that workflow(s) and workflow step(s) are conducted by the clinical diagnostic system.

In particular, the controller may communicate and/or cooperate with a scheduler and/or data manager in order to take into account incoming analysis orders and/or received analysis orders and a number of scheduled process operations associated with the execution of the analysis orders in order to decide when and which test sample has to be prepared and for each sample when and which preparation step has to be executed. As different types of samples and/or different analytes of interest contained in the same or different types of samples may require different preparation conditions, e.g., different reagents, or different number of reagents, different volumes, different incubation times, different washing conditions, and the like, preparation of different samples may require different sample preparation workflows. The controller may thus be programmed to assign samples to pre-defined sample preparation workflows each comprising a pre-defined sequence of sample preparation steps, including e.g., different steps and/or a different number of steps, and requiring a pre-defined time for completion, e.g., from a few minutes to several minutes.

The controller may schedule sample preparation to occur in parallel or in a staggered manner for different samples. By doing so in a logical manner, the controller can schedule the use of functional resources of the sample preparation station in order to increase efficiency while avoiding conflicts and maximizes throughput by preparing samples at a pace at which prepared samples can be inputted into the LC separation station. Thus, rather than preparing a batch of samples in advance, which of course is also possible, the controller can instruct the sample preparation station to prepare samples as needed or as can be taken from the LC separation station, in particular, by the individual LC channels, while taking into account incoming orders, e.g., priority orders, time of preparation, required use of functional resources, availability of the LC channel for which that sample is intended by the time sample preparation is completed.

An "operational parameter" can be a measurable property, or a property derivable from raw data, including any sort of distinguishable physical and/or chemical signal, that can be detected and quantified during operation of the clinical diagnostic system such as but not limited to electrical current, voltage, electrical resistance, electrical capacitance, magnetic field, time, distance, size, shape, area, volume, height, velocity, position, temperature, pressure, viscosity, pH, surface properties, chemical and/or biological properties, mechanical resistance, light intensity, wavelength, frequency, noise, and the like. The term "raw data" that may be also called "source data" can be data that has not been processed for use, but has the potential to become information by selective extraction, organization, and sometimes analysis and formatting for presentation. Once processed, the data can become an operational parameter. In particular, a set of operational parameters can be selected that if monitored can be indicative of the performance status of the clinical diagnostic system in general and in particular of the individual modules and even individual functional (operational) components of the different modules of the clinical diagnostic system.

The term "operation" or "operational" can include any time during which the clinical diagnostic system is occupied at processing samples or during which it is occupied with a quality or maintenance procedure or during which it is in an idle or standby status as long as monitoring of the predetermined set of operational parameters or at least a subset of the predetermined set of operational parameters can take place and the controller is active.

The "monitoring" of the operational parameters may be continuous or at intervals and may occur simultaneously or at different or at overlapping times depending on the particular parameters and actual operational status. In particular, not all operational parameters of the set of operational parameters may need to be monitored at the same time and at any given time. For example, monitoring of some operational parameters may occur only when some functional components of the clinical diagnostic system are active. In particular, monitoring of at least some operational parameters may be paused and resumed or simply ignored by the controller depending on the particular actual operational status.

The term "performance status" can refer to the ability of the clinical diagnostic system to achieve its intended purpose as specified by the manufacturer and to ensure analytical performance, i.e., the ability to correctly detect and/or measure analytes of interest. Thus, the term "indicative of the performance status" with reference to the set of operational parameters can mean determining or at least contributing to determine (indicating) whether the clinical diagnostic system is performing or non-performing according to specification.

In particular, the controller can be programmed to trigger a quality control procedure and/or a maintenance procedure whenever one or more parameters of the predetermined set of operational parameters is out of specification and to minimize the quality control and/or maintenance procedures as long as the set of operational parameters remains within specification.

A "quality control procedure" or "QC procedure" can be a procedure intended to check or to make sure that the clinical diagnostic system meets the specified analytical performance. The QC procedure can herein therefore be used to intend any one or both of a calibration procedure using one or more calibrators and a check with one or more QC samples, by running one or more QC samples, unless explicitly stated.

A "maintenance procedure" can be a procedure intended to investigate a root cause of a technical issue responsible for an operational parameter to be out of specification and/or to resolve an identified technical issue and/or a preventive measure intended to prevent that a technical issue occurs. The maintenance procedure may comprise actions such as checking, adjusting, correcting, cleaning, repairing, replacing, and the like.

The term "trigger" or "triggering" can herein be used to intend either an automatic procedure that is initiated by the controller and executed by the clinical diagnostic system automatically or a warning generated by the controller and prompting a user to manually intervene or a semiautomatic procedure as a combination of both. The execution of the triggered procedure may not be limited to a particular time. It may occur soon or at a later convenient time depending also on the severity of the event and/or on the operational parameter that is out of specification and/or on the degree of deviation from specification. Also, quality control and maintenance procedures may be scheduled and manually initiated at any time regardless of a trigger event.

The term "according to specification" or "within specification" can refer to a range or a threshold specified by the manufacturer that can have a measurable value and within which or below or above which an operational parameter is supposed to be in order for the clinical diagnostic system to achieve its intended purpose and to ensure analytical performance. This may include also a tolerance range within which, although the operational parameter is out of specification, it can be considered still acceptable. The specification range or threshold and eventual tolerance ranges may be different for different operational parameters and, also, the measurement units may be different.

The term "out of specification" can have the opposite meaning of the term "within specification".

"Minimizing the quality control and/or maintenance procedures" may comprise increasing the time in between regularly scheduled (routine) quality control and/or maintenance procedures and/or reducing the number of regularly scheduled (routine) quality control and/or maintenance procedures, e.g., compared to the number and frequency of routine procedures as suggested by reference laboratory guidelines, in absence of trigger events, i.e., as long the set of operational parameters remains within specification. It may also, or in alternative, comprise performing a minimum or lower level of quality control, for example, by running a QC sample through only one or fewer LC channels out of a plurality of LC channels rather than through each of the plurality of LC channels and/or by using only one or fewer QC substances as lead/proxy QC substances with respect to a group of similar analytes of interest, e.g., having similar log P value and/or m/z value. It may also, or in alternative, comprise using QC samples or QC substances according to a predetermined hierarchy, where quality control procedures at lower hierarchical levels may be quicker and more convenient in terms of use of system resources and materials, although eventually meeting lower quality standards compared to quality control procedures at higher hierarchical levels. Also, quality control procedures at lower hierarchical levels may occur more frequently than quality control procedures at higher hierarchical levels or even continuously, e.g., in the background while processing test samples.

According to an embodiment, quality control procedures can comprise the following hierarchical levels from lowest to highest: tracking of system fluids/reagents, tracking of QC substances contained in reagents as internal standards, tracking of QC substances added to samples or sample/reagent mixtures during sample preparation as internal standards, running of dedicated QC samples.

In particular, tracking of system fluid/reagents may include monitoring background signal intensity and/or slope of background signal line due to reagents and/or system fluids used, e.g., eluents used in the LC separation station, or any other fluids used for washing and like, during test sample processing and detection of analytes of interest or even during idle time or maintenance time.

Tracking of QC substances contained in reagents may comprise detecting and assessing the shape of LC and/or MS peaks of such QC substances when using such reagents, e.g., peak symmetry, peak width at half maximum, peak area and borders, elution/retention time, ratio of adjacent peak heights, signal/noise ratio, m/z value of peak maximum, and the like. The QC substances may be added to the reagents at manufacturing, and may be present in any number and combination, e.g., forming a chemical code that may be different for each reagent or reagent type and can be used also for identifying reagents. Also, they can be present in a sufficiently low concentration that can be detected only after concentration during sample processing.

Tracking of QC substances added to samples or sample/reagent mixtures may comprise detecting and assessing the shape of LC and/or MS peaks of such added QC substances, e.g., peak symmetry, peak width at half maximum, peak area and borders, elution/retention time, ratio of adjacent peak heights, signal/noise ratio, m/z value of peak maximum, and the like. The QC substances may be added to samples or sample/reagent mixtures during sample preparation in any number and combination, e.g., forming a chemical code that can be used for example also to track test samples being processes in parallel, e.g., to confirm that an analyte being detected by the mass spectrometer comes from a particular prepared sample injected into one of the LC channels. According to an embodiment, the QC substances can comprise isotopically labelled analogs of analytes of interest.

Dedicated QC samples may be also subdivided in different hierarchical levels, e.g., based on a surrogate matrix or on a human matrix, e.g., comprising a QC substance for each analyte of interest, e.g., at different concentrations, or only one or fewer QC substances for a larger group of analytes of interest having similar characteristics, e.g., similar log P value and/or m/z value.

At least some quality control procedures of different hierarchical levels may occur in parallel in order to meet higher quality standards.

Thus the controller, by monitoring the predetermined set of operational parameters, can try to minimize quality control and/or maintenance procedures as much as possible in order to free more time and functional resources for processing test samples.

According to an embodiment, the predetermined set of operational parameters can comprise a first subset based on data from the result calculation module, typically generated while elaborating LC/MS signals, e.g., for identifying and/or quantifying analytes or substances of interest contained in samples or reagents, or while monitoring background signals, and in a second subset based on raw data from the sample preparation module, LC separation module and MS module, that can be generated at any time during operation, including idle/standby time, maintenance time, and the like and typically not used or taken into account by the result calculation module for identifying and/or quantifying analytes of interest.

According to an embodiment, the controller, following a passed quality control procedure, can be programmed to trigger one or more of a further quality control procedure and/or maintenance procedure whenever one or more parameters of the first subset of operational parameters is out of specification and to minimize further quality control and/or maintenance procedures as long as the first subset of operational parameters remains within specification.

According to an embodiment, whenever one or more parameters of the first subset of operational parameters is out of specification, the controller can be programmed to check the raw data of the second subset of operational parameters and to trigger one or more of a further quality control procedure and/or maintenance procedure whenever one or more parameters of the second subset of operational parameters is out of specification and to minimize further quality and/or maintenance procedures as long as the second subset of operational parameters remains within specification.

According to an embodiment, the first subset of operational parameters can comprise at least one of shape of LC and/or MS peaks, such as peak symmetry, peak width at half maximum, peak areas and borders, analyte elution/retention time, ratio of adjacent peak heights (isotopic pattern), signal/noise ratio, analyte signal intensity, background signal intensity, slope of background signal line, m/z value of peak maximum, m/z mass accuracy, calculated concentration of analyte, calculated concentration of QC substance. The list is not exhaustive.

According to an embodiment, the peaks can be one or a plurality of any one or more of an analyte peak, an analyte fragment peak or isotope peak, a QC substance peak or reference substance peak added to a sample or to a reagent, or a fragment peak thereof or isotope peak thereof.

According to an embodiment, depending on the operational parameter or parameters that are out of specification, the one or more quality control and/or maintenance procedures can comprise any one or more of running a calibration procedure and/or a QC sample, adjusting any one or more of LC conditions such as elution gradient, flow rate, pressure and temperature, changing eluents, regenerating or replacing an LC column, re-initialization of the MS module, tuning and calibration of the MS module, adjusting any one or more of the MS conditions such as adjusting of voltages, of gas pressure and temperature in ion source, cleaning of any parts of the sample preparation module, LC module, MS module, checking and eventually replacing a QC sample. The list is not exhaustive.

According to an embodiment, the second subset of operational parameters related to the sample preparation module can comprise raw data with respect to at least one of power/energy consumption and/or voltage/amperage of electrically powered functional units, such as a cooling device, an electric motor, a vacuum pump, and the like, linear and/or rotational velocity and/or position of drive units and/or driven functional units, e.g., angular and/or linear drive step loss of one-, two- or three-dimensional drive units, e.g., pipetting units/probes, mixing units, grippers, liquid level detectors, and the like, velocity of pipetting strokes, aspiration and/or dosing velocity, rotational speed of mixing paddle, pressure in fluidic system, e.g., in pipettor tubing and/or pipetting tip/probe. The list is not exhaustive.

According to an embodiment, depending on the operational parameter or parameters that are out of specification, the one or more quality control and/or maintenance procedures can comprise any one or more of running a calibration procedure and/or a QC sample, repairing or exchanging drive units and/or driven functional units or parts thereof, checking for leakage or loose connections and eventually replacing fittings or tightening, checking for clogging, for presence of foam or clot in samples or air in the fluidic system and eventually running an event specific protocol, checking for correct positioning of consumables, e.g., reagent or sample containers, or for sufficient test fluid volume and eventually exchanging or replacing consumables, checking alignment of drives and eventually re-adjusting alignment. The list is not exhaustive.

According to an embodiment, the second subset of operational parameters related to the LC separation module can comprise raw data with respect to at least one of liquid pressure, e.g., LC pump back pressure, gas pressure, e.g., degasser pressure, temperature, flow rate, consumable level, waste level, power/energy consumption and/or voltage/amperage of electrically powered functional units, e.g., pumps, switching valves, and the like, linear and/or rotational velocity and/or position of drive units and/or driven functional units, e.g., pumps, switching valves, injector, and the like. The list is not exhaustive.

According to an embodiment, depending on the operational parameter or parameters that are out of specification, the one or more quality control and/or maintenance procedures can comprise any one or more of running a calibration procedure and/or a QC sample, checking for leakage or loose connections and eventually replacing fittings or tightening, replacing or refilling eluents, regenerating or replacing an LC column, checking and eventually repairing or replacing a heater, checking and eventually repairing or replacing valves or pumps. The list is not exhaustive.

According to an embodiment, the second subset of operational parameters related to the MS module can comprise raw data with respect to at least one of gas pressure, gas temperature, applied voltages and currents, flow rates, radio frequency, e.g., with respect to the ion source, mass analyzer or ion detector. The list is not exhaustive.

According to an embodiment, depending on the operational parameter or parameters that are out of specification, the one or more quality control and/or maintenance procedures can comprise any one or more of running a calibration procedure and/or a QC sample, checking ionization source clean status, re-tuning of MS module, re-initialization of the MS module, checking and eventually repairing or replacing a flow meter, checking and eventually repairing or replacing an ionization source heater, checking and eventually repairing or replacing a control board. The list is not exhaustive.

Tuning of the MS module may comprise adjusting electrical settings and/or temperature and/or gas flow rates of the mass spectrometer ion source, of the mass analyzers, e.g., of quadrupoles, time of flight or ion trap, of the collision cell and/or of the ion detector, e.g., of electron multiplier voltage. The list is not exhaustive.

A "flow meter" can be a device for measuring liquid flow velocity (eluent flow from LC column) or gas flow (nitrogen, argon, air).

Regardless of the embodiment, depending on the operational parameter or parameters that are out of specification, the controller may be programmed to prevent queueing up samples, for which a test order has been received but processing has not yet started, from entering the clinical diagnostic system and/or from starting the sample preparation process by the sample preparation module. Otherwise, if sample processing has already started, the controller may be programmed to prevent samples from being further processed, e.g., by interrupting the current process or by preventing the samples to advance to the next module, e.g., to the LC separation module and/or MS module. The controller may be further programmed to trigger a system and/or module stop or to set the system and/or a module in an idle/standby mode until the one or more parameters remain out of specification and/or as long as the triggered quality control and/or maintenance procedure has not been executed.

In this way, unnecessary consumption of samples and consumables, including reagents, can be prevented, generation of erroneous results can be prevented, damages of the system or system modules can be prevented, and safety of operation can be increased.

An interconnected laboratory system is herein also disclosed, comprising a plurality of clinical diagnostic systems according to any of the above embodiments.

The interconnected laboratory system can further comprise a central data receiving device and a central controller.

A "central data receiving device" can be a data storage device that can be remotely connected, e.g., via a wired or wireless network, e.g., embodied as a server or cloud, with a plurality of clinical diagnostic systems for receiving data from the plurality of clinical diagnostic systems and communicating with the central controller.

In particular, the central data receiving device can be configured to receive data from the monitoring of the predetermined set of operational parameters from the plurality of clinical diagnostic systems.

A "central controller" can be a controller that is connected to the central data receiving device, e.g., via a wired or wireless network, and can be programmed to compare data from different clinical diagnostic systems and/or from one or more clinical diagnostic systems with data from one or more reference clinical diagnostic systems. The central controller can further be programmed to trigger one or more of a quality control procedure and/or maintenance procedure, with respect to any of the clinical diagnostic systems whenever its performance status deviates from the performance status of the other clinical diagnostic system or systems it is compared to, and/or to adjust one or more specification ranges for any of the operational parameters of any one or more of the clinical diagnostic systems.

Data received from multiple clinical diagnostic systems and comparison of such data may be also used for proactive customer service, e.g., to inform a user of the current performance status of a clinical diagnostic system, and remotely trigger maintenance procedures, including preventive maintenance procedures, e.g., based on comparison with the performance status of other clinical diagnostic systems.

Also, issue tracking, complaint handling and customer care in general can be facilitated.

A clinical diagnostic method is herein also disclosed. The method can comprise monitoring a predetermined set of operational parameters indicative of a performance status of a clinical diagnostic system according to any of the above embodiments. The method can further comprise triggering a quality control procedure and/or a maintenance procedure whenever one or more parameters of the predetermined set of operational parameters is out of specification and minimizing the quality control and/or maintenance procedures as long as the set of operational parameters remains within specification.

With reference to FIG. 1, an example of clinical diagnostic system 100 is schematically described. The clinical diagnostic system 100 can comprise a sample preparation module 20 for the automated preparation of samples, a liquid chromatography (LC) separation module 30 coupled to the sample preparation module 20 via a sample preparation/LC interface 40, a mass spectrometer (MS) module 50 coupled to the LC separation module 30 via an LC/MS interface 60, and a result calculation module 70 for identifying and/or quantifying analytes or substances of interest contained in the samples and passed through the LC separation module 30 and the MS module 50. The result calculation module 70 can thus be directly connected at least with the MS module 50.

The sample preparation/LC interface 40 may be embodied as another individual module or as part of the sample preparation module 20 or as part of the LC separation module 30 or both. Analogously, the LC/MS interface 60 may be embodied as another individual module or as part of the LC separation module 30 or as part of the MS module 50 or both.

The clinical diagnostic system 100 can further comprise a controller 80. The controller 80 is programmed to monitor a predetermined set of operational parameters 1-$n$ indicative of a performance status of the clinical diagnostic system 100. The operational parameters 1-$n$ are typically different for each module 20, 30, 50, 70. In particular, the sample preparation module 20 comprises its own predetermined set 21 of operational parameters 1-$n$, indicative of the performance status of the sample preparation module 20. The LC separation module 30 comprises its own predetermined set 31 of operational parameters 1-$n$, indicative of the performance status of the LC separation module 30. The MS module 50 comprises its own predetermined set 51 of operational parameters 1-$n$, indicative of the performance status of the MS module 50. The predetermined sets 21, 31 of operational parameters from the sample preparation module 20 and LC separation module 30 respectively, may comprise one or more operational parameters from the sample preparation/LC interface 40 as well, that are indicative of the performance status of the sample preparation/LC interface 40. Analogously, the predetermined sets 31, 51 of operational parameters from the LC separation module 30 and MS module 50 respectively, may comprise one or more operational parameters from the LC/MS interface 60 as well, that are indicative of the performance status of the LC/MS interface 60. The result calculation module 70 comprises its own predetermined set 71 of operational parameters 1-$n$ that may be indicative of the performance status of any of the sample preparation module 20, the LC separation module 30, the MS module 50 and the clinical diagnostic system 100 in general. According to an embodiment, the predetermined set 71 of operational parameters 1-$n$ from the result calculation module 70 represent a first subset whereas the predetermined sets 21, 31, 51 of operational parameters 1-$n$ from the sample preparation module 20, LC separation module 30 and MS module 70 respectively represent a second subset.

The controller 80 can further be programmed to minimize the quality control and/or maintenance procedures as long as the sets 21, 31, 51, 71 of operational parameters 1-$n$ remain within specification, e.g., by executing only regularly scheduled (routine) QC procedures 1-$n$, e.g., before and after analyzing a series of samples S1-$n$.

The controller 80 can further be programmed to trigger a quality control procedure and/or a maintenance procedure whenever one or more parameters 1*, 2* of the predetermined sets 21, 31, 51, 71 of operational parameters 1-$n$ from any of the modules 20, 30, 50, 70, including the sample preparation/LC interface 40 and the LC/MS interface 50 is out of specification.

The controller 80 may be further programmed to assign samples to pre-defined sample preparation workflows, each comprising a pre-defined sequence of sample preparation steps and requiring a pre-defined time for completion depending on the analytes of interest. In particular, the controller 80 may be further programmed to assign (reserve in advance) an LC channel for each prepared sample depending on the analytes of interest and to plan an LC channel input sequence for inputting the prepared samples that allows analytes of interest from different LC channels to elute in a non-overlapping LC eluate output sequence based on expected elution times. The controller 80 may be further programmed to set and initiate a sample preparation start sequence that generates a prepared sample output sequence that matches the LC channel input sequence.

In FIG. 1, each LC eluate of the LC eluate output sequence S1-$n$ can be indicated in a segment of a sequence comprising non-overlapping adjacent segments, each segment representing schematically a reference time period of equal length. Each sequence can thus be a sequence of reference periods or time units, the length of which can be fixed and can remain constant across different sequences. Preparation of new samples in the sample preparation start sequence can be started with a frequency of one sample per reference period, or at intervals separated by one or more reference periods, in which no sample preparation is started. Also, preparation of samples in the prepared sample output sequence can be completed with a frequency of one prepared sample per reference period or at intervals separated by one or more reference periods, in which no sample preparation is completed. Also, the prepared samples can be inputted in the respective assigned LC channels according to the LC channel input sequence with a frequency of one LC channel input per reference period or at intervals separated by one or more reference periods, in which no LC channel input takes place.

Finally, as indicated in FIG. 1, the LC eluates in the LC eluate output sequence S1-$n$ can be outputted with a frequency of one LC eluate per reference period or at intervals separated by one or more reference periods, indicated by empty segments in the sequence, in which no LC eluate is outputted.

By monitoring the predetermined set 21, 31, 51, 71 of operational parameters 1-$n$ indicative of a performance status of the clinical diagnostic system 100, it can be possible to identify at any time, during result calculation but also during empty segments in the sequence and even during idle or standby time of the clinical diagnostic system 100 if one or more parameters 1-$n$ are out of specification and to trigger a QC and/or maintenance procedure accordingly. Importantly, it can be prevented that once any of such sample processing sequences, including sample preparation start sequence, LC channel input sequence, LC eluate output sequence is planned and/or initiated is then interrupted as long as the set of operational parameters 1-$n$ remain within specification. Thus, higher throughput can be achieved and even longer sequences can be scheduled.

With continued reference to FIG. 1, a clinical diagnostic method is also illustrated. The method can comprise monitoring a predetermined set 21, 31, 51, 71 of operational parameters 1-$n$, indicative of a performance status of a clinical diagnostic system 100, triggering a quality control procedure and/or a maintenance procedure whenever one or more parameters 1-$n$ of the predetermined set 21, 31, 51, 71 of operational parameters 1-$n$ is out of specification, and minimizing the quality control and/or maintenance procedures as long as the set 21, 31, 51, 71 of operational parameters 1-*n* remains within specification.

Figure 2:
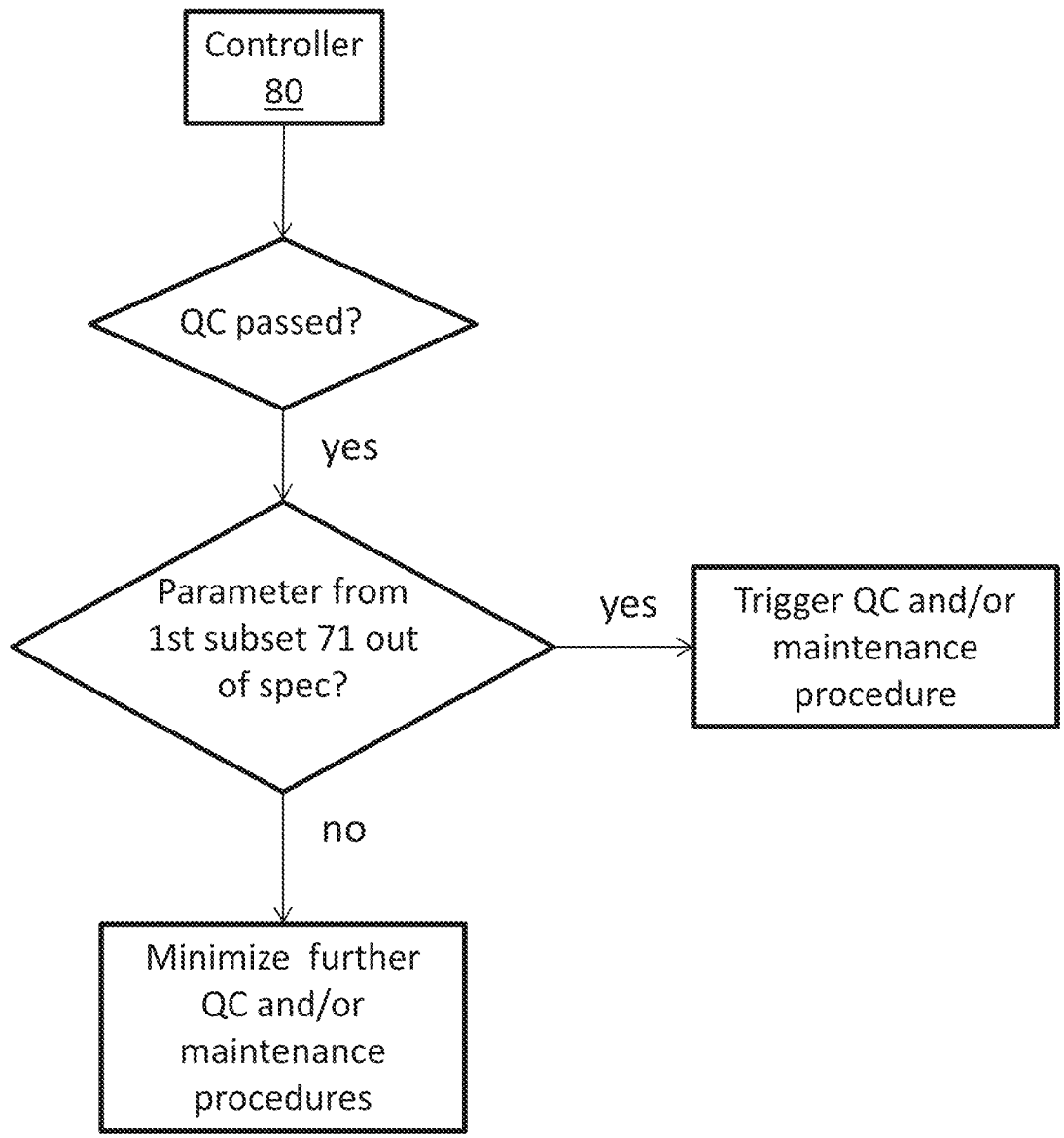
FIG. 2 illustrates schematically to an embodiment of the clinical diagnostic system of FIG. 1 according to an embodiment of the present disclosure.

According to an embodiment schematically shown in FIG. 2, the controller 80, following a passed quality control procedure, can be programmed to trigger one or more of a further quality control procedure and/or maintenance procedure whenever one or more parameters of the first subset 71 of operational parameters is out of specification and to minimize further quality control and/or maintenance procedures as long as the first subset 71 of operational parameters remains within specification.

Figure 3:
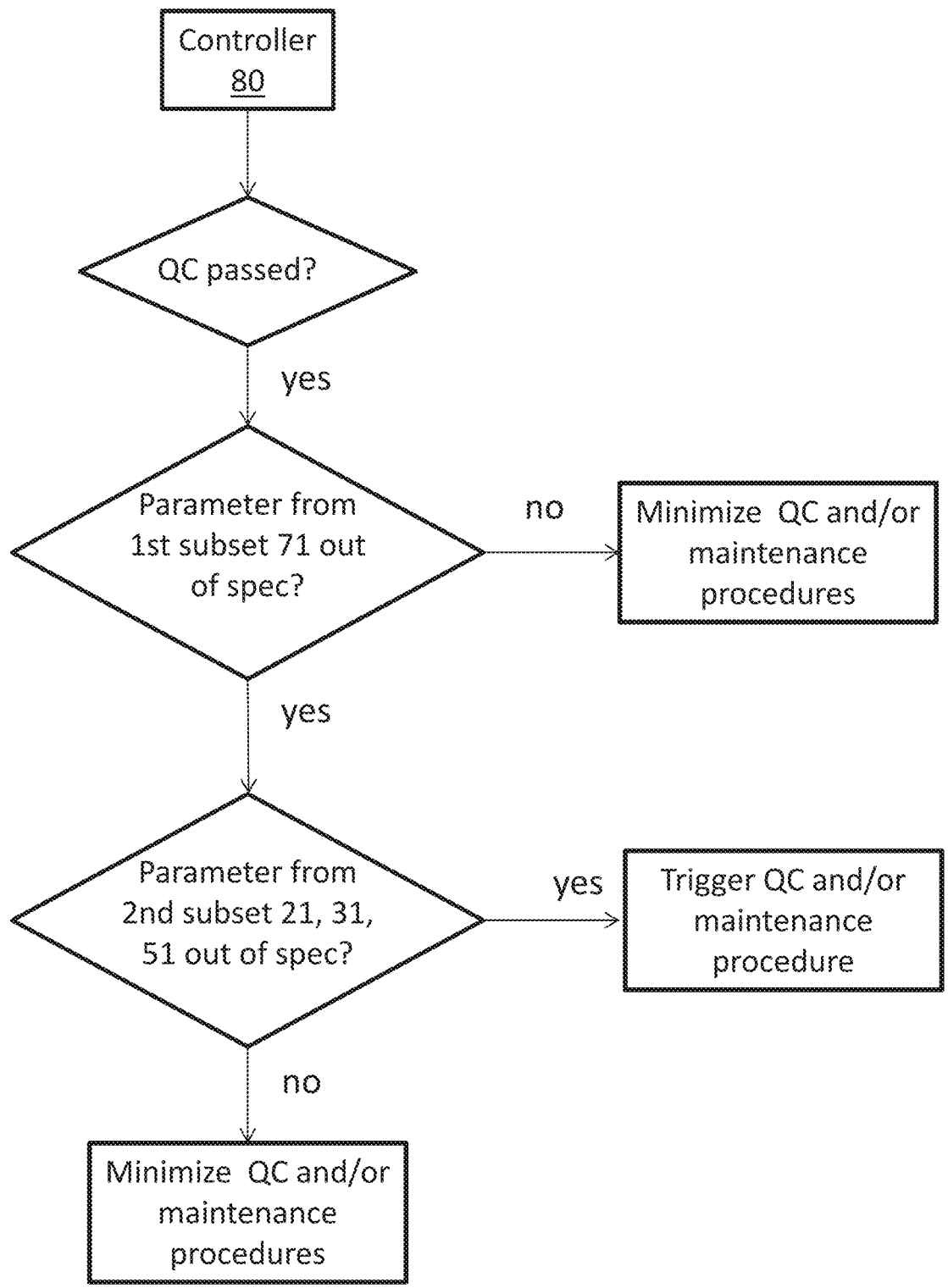
FIG. 3 illustrates schematically to a variant of the embodiment of FIG. 2 according to an embodiment of the present disclosure.

According to an embodiment schematically shown in FIG. 3, which is a variant of the embodiment of FIG. 2, whenever one or more parameters of the first subset 71 of operational parameters is out of specification, the controller 80 can be programmed to check the raw data of the second subset 21, 31, 51 of operational parameters and to trigger one or more of a further quality control procedure and/or maintenance procedure whenever also one or more parameters of the second subset 21, 31, 51 of operational parameters is out of specification, while minimizing further quality and/or maintenance procedures as long as the second subset 21, 31, 51 of operational parameters remains within specification. In this way, it can be determined and/or confirmed if a failure or problem occurs at any of the sample preparation module 20, LC separation module 30, MS module 50, including sample preparation/LC interface 40 and LC/MS interface 60, and a more appropriate (targeted) quality control and/or maintenance procedure can be triggered. Also, as far as the first subset 71 of operational parameters remains within specification it may be sufficient for the controller 80 to take only the operational parameters from the first subset 71 into account in order to avoid being overloaded with check and calculation operations that are not necessarily needed all the time. It can otherwise also be possible to take fewer rather than all operational parameters of the second predetermined subset 21, 31, 51 into account.

FIG. 4 shows for illustration purpose only, as one of an infinite number of possible examples, a table with measured/calculated numerical values and reference specification ranges for a selected number of operational parameters from the result calculation module, hence from the first subset 71 of operational parameters. One operational parameter can be the retention time of an analyte of interest, measured in minutes (min), with the specification range indicated in parenthesis. Another operational parameter can be the mass resolution, with reference to the full width at half maximum (FWHM) of the MS peaks, and with the specification range indicated in parenthesis. Another operational parameter can be the absolute intensity, measured in counts per second (cps), with the specification range indicated in parenthesis. Another operational parameter can be the accurate mass error, measured in parts per million (ppm), with the specification range indicated in parenthesis. In particular, for a series of samples 1-27, the same (4 in this case) operational parameters can be monitored with respect to the same analyte of interest (for simplicity). Based on the observation of whether one or more of the operational parameters are out of specification or not, the controller may trigger a specific QC and/or maintenance procedure as an indicated in an action column of the table.

Figure 5:
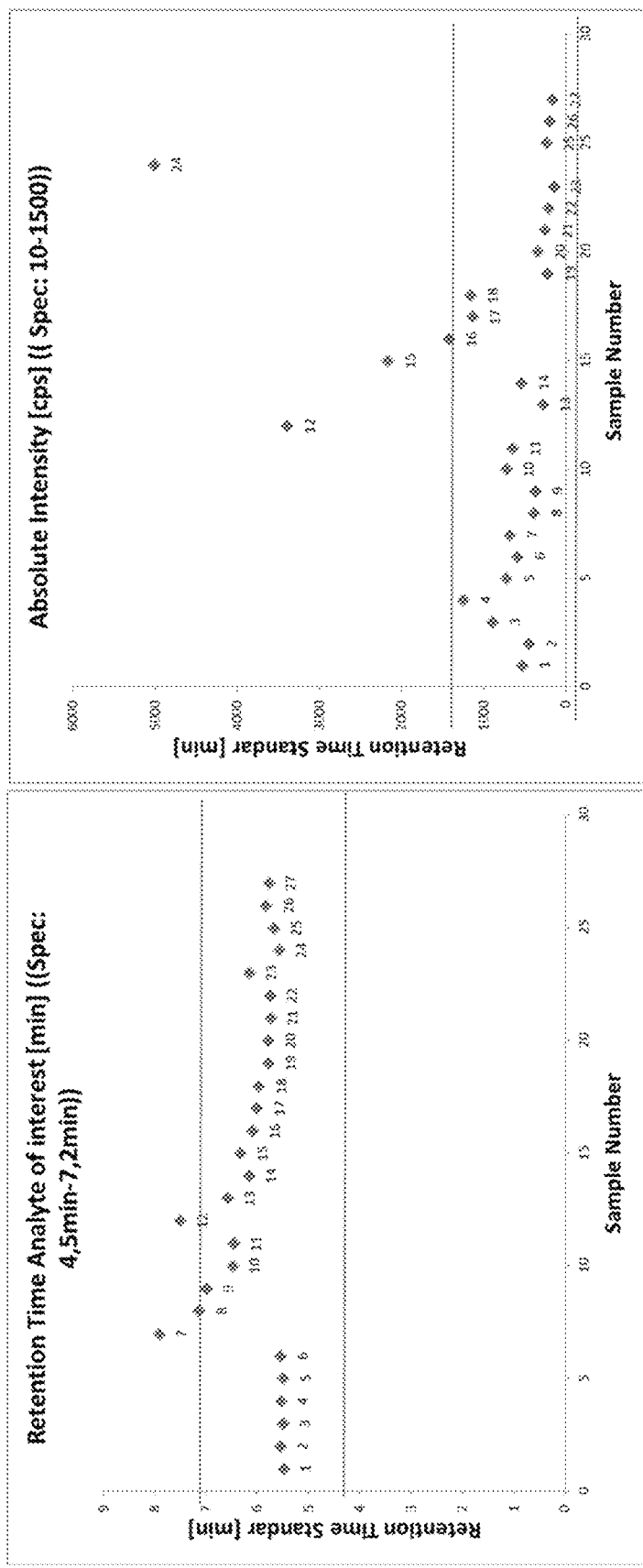
FIG. 5 illustrates a partial graphical representation of the table of FIG. 4 according to an embodiment of the present disclosure.
Figure 6:
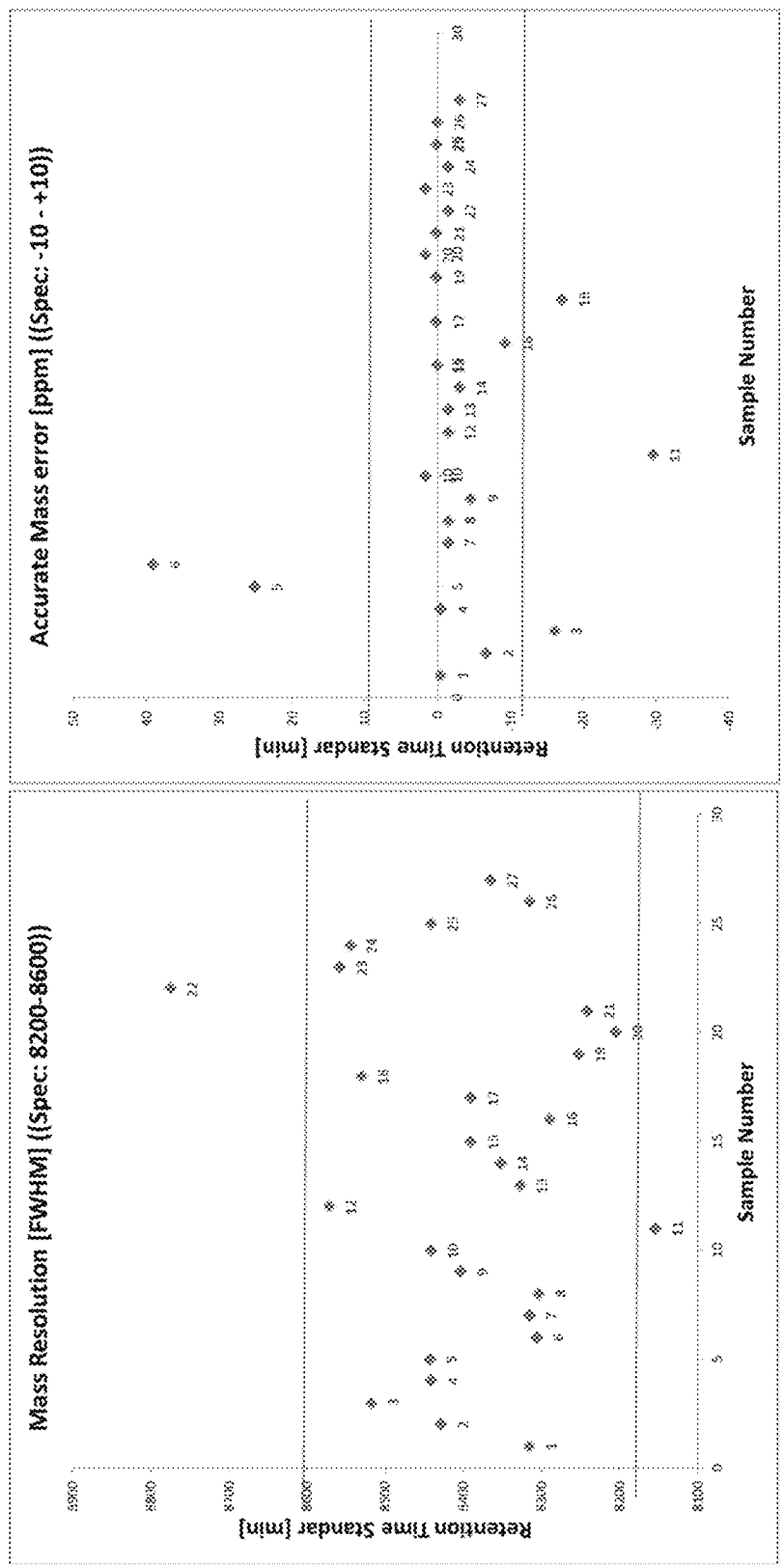
FIG. 6 illustrates a partial graphical representation of the table of FIG. 4 according to an embodiment of the present disclosure.

FIG. 5 and FIG. 6 are only graphical representations of the numerical values of the table of FIG. 3 for each of the individual operational parameters.

The first subset 71 of operational parameters 1-*n* from the result calculation module 70 may otherwise comprise at least one of shape of LC and/or MS peaks, analyte elution/retention time, ratio of adjacent peak heights, signal/noise ratio, analyte signal intensity, background signal intensity, slope of background signal line, m/z value of peak maximum, m/z mass accuracy, calculated concentration of analyte, calculated concentration of QC substance. Also, the quality control and/or maintenance procedures triggered as an action may comprise any one or more of running a calibration procedure and/or a QC sample, adjusting any one or more of LC conditions such as elution gradient, flow rate, pressure and temperature, changing eluents, regenerating or replacing an LC column, re-initialization of the MS module, tuning and calibration of the MS module, adjusting any one or more of the MS conditions such as adjusting of voltages, of gas pressure and temperature in ionization source, cleaning of any parts of the sample preparation module, LC module, MS module, checking and eventually replacing a QC sample.

Figure 7:
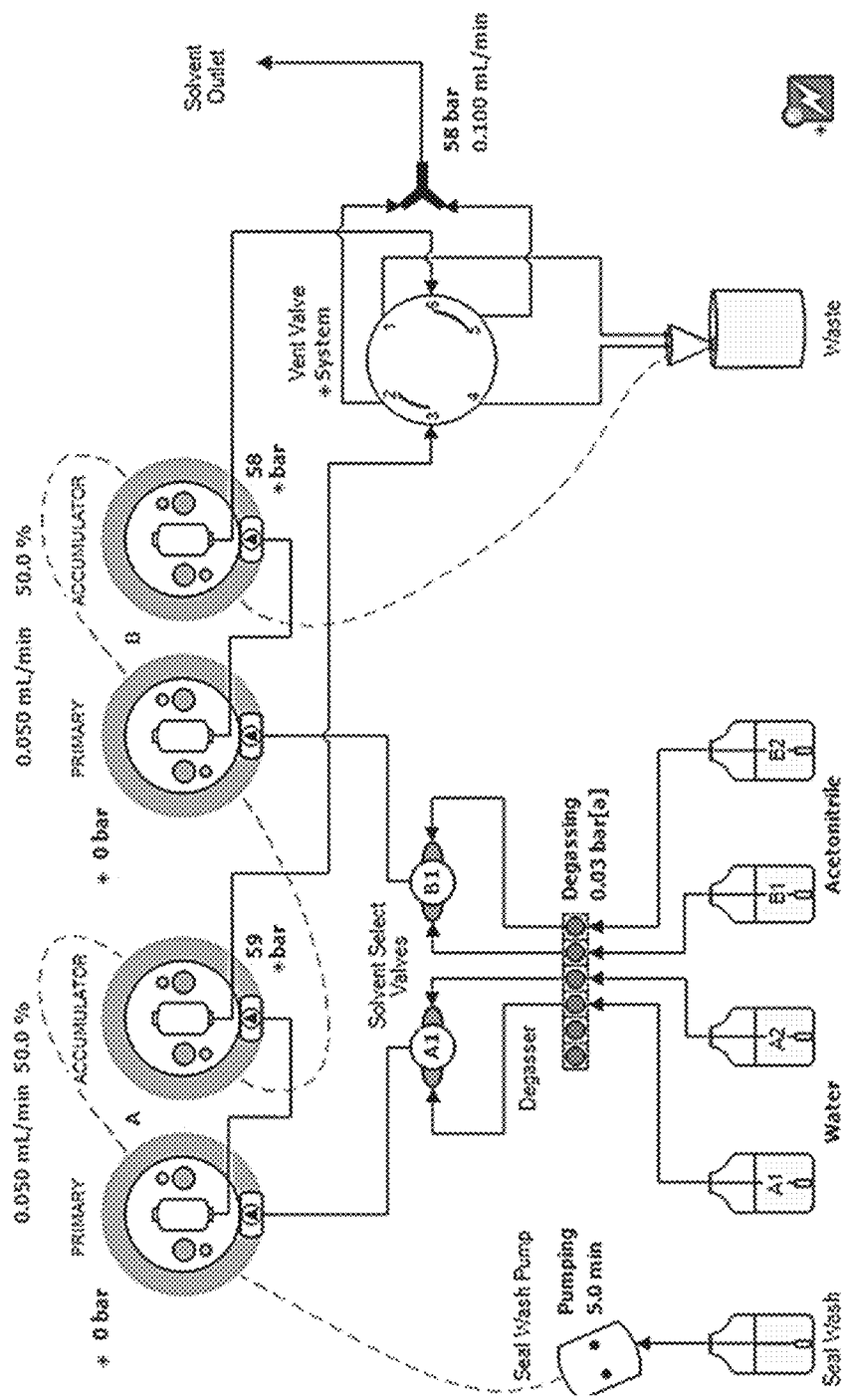
FIG. 7 illustrates schematically examples of operational parameters of the LC separation module according to an embodiment of the present disclosure.

FIG. 7 shows for illustration purpose only, as one of possible examples, a schematic representation of some of the components of the LC separation module 30 of FIG. 1, together with some of the operational parameters of the LC separation module 30 that can be monitored, like fluidic pressure (in bar) at different locations, gas pressure at the degasser (in bar), flow rate of the pumps (in mL/min).

Figure 8:
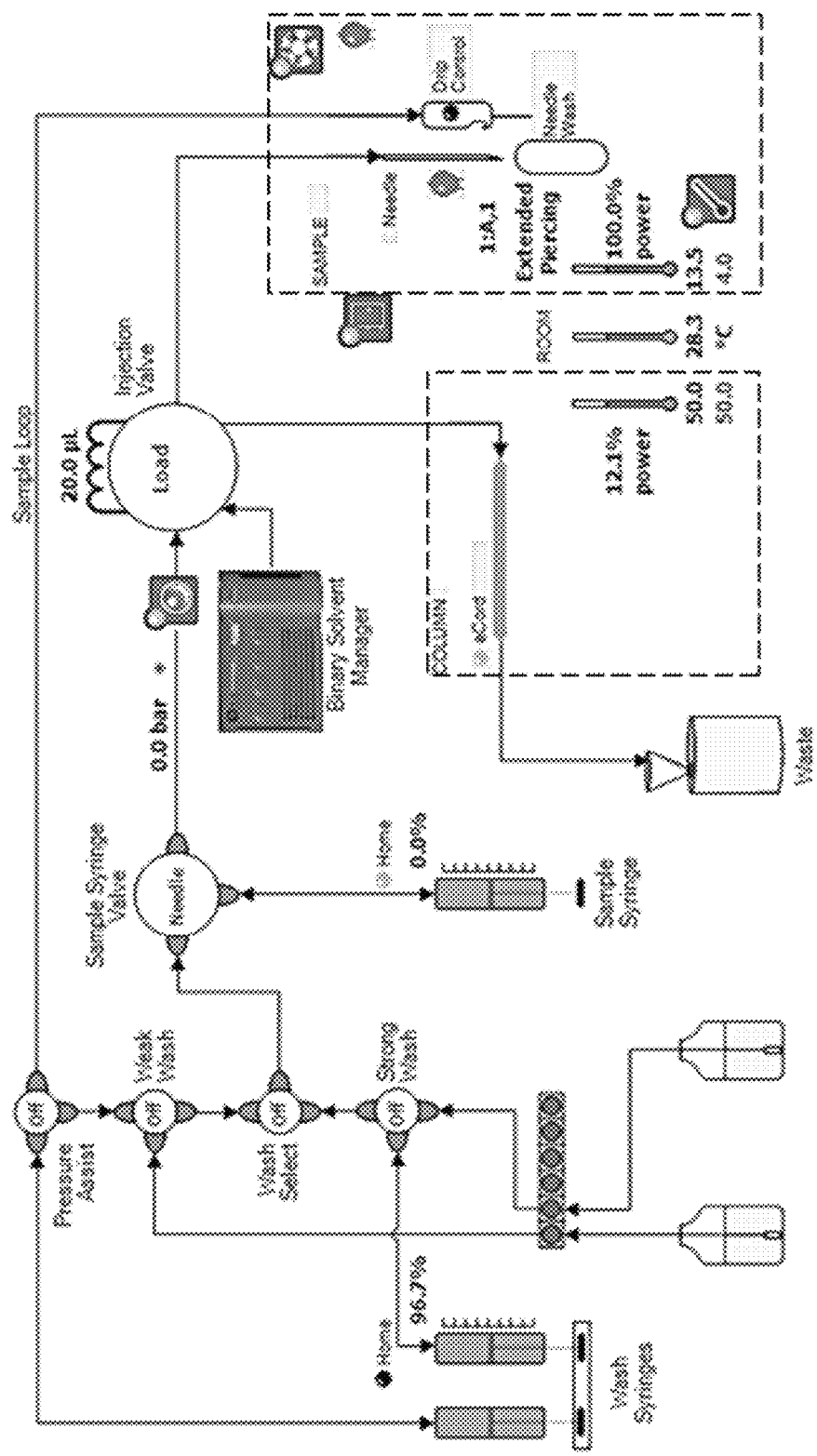
FIG. 8 illustrates schematically other examples of operational parameters of the LC separation module according to an embodiment of the present disclosure.

FIG. 8 that is complementary to FIG. 7 shows for illustration purpose only, as one of possible examples, a schematic representation of some other components of the LC separation module 30 together with some other operational parameters of the LC separation module 30 that can be monitored, like temperature at the separation column, temperature at the sample injection and room temperature for simplicity.

Otherwise, the operational parameters from the LC separation module 30 may comprise raw data with respect to at least one of liquid pressure, gas pressure, temperature, flow rate, consumable level, waste level, power/energy consumption and/or voltage/amperage of electrically powered functional units, linear and/or rotational velocity and/or position of drive units and/or driven functional units. Although not shown in the figure, the one or more quality control and/or maintenance procedures may comprise any one or more of running a calibration procedure and/or a QC sample, checking for leakage or loose connections and eventually replacing fittings or tightening, e.g. if liquid or gas pressure is out of specification, replacing or refilling eluents, regenerating or replacing an LC column, checking and eventually repairing or replacing a heater, e.g. if the temperature is out of specification, checking and eventually repairing or replacing valves or pumps.

Figure 9:
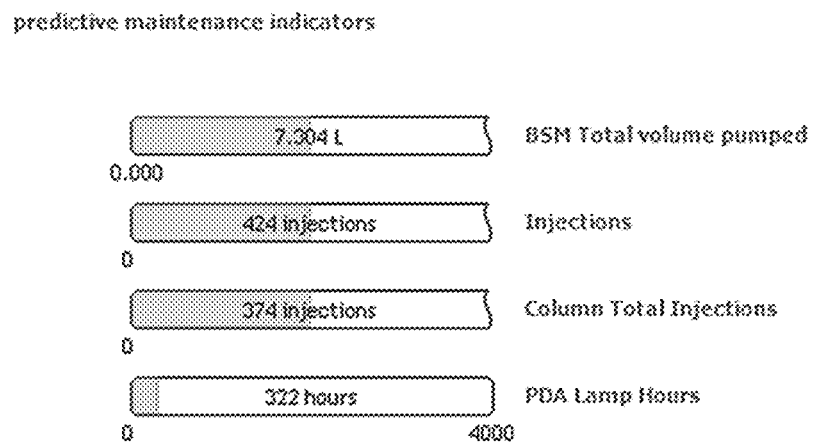
FIG. 9 illustrates schematically other examples of operational parameters of the LC separation module according to an embodiment of the present disclosure.

FIG. 9 shows schematically and for illustration purpose only another example of operational parameters that may be particularly useful for triggering a preventive maintenance procedure. In this example, predictive maintenance indicators such as pumped volumes, number of injections, number of LC runs using the same LC column, number of hours a lamp or other functional component was used and the like may be monitored (counted) in order to predict when a preventive maintenance procedure, like a replacement or cleaning, may be due and triggered before an actual failure event or issue occurs. Similar or analogous operational parameters may be monitored for the sample preparation module and for the MS module as well (not shown).

Figures 10, 11:
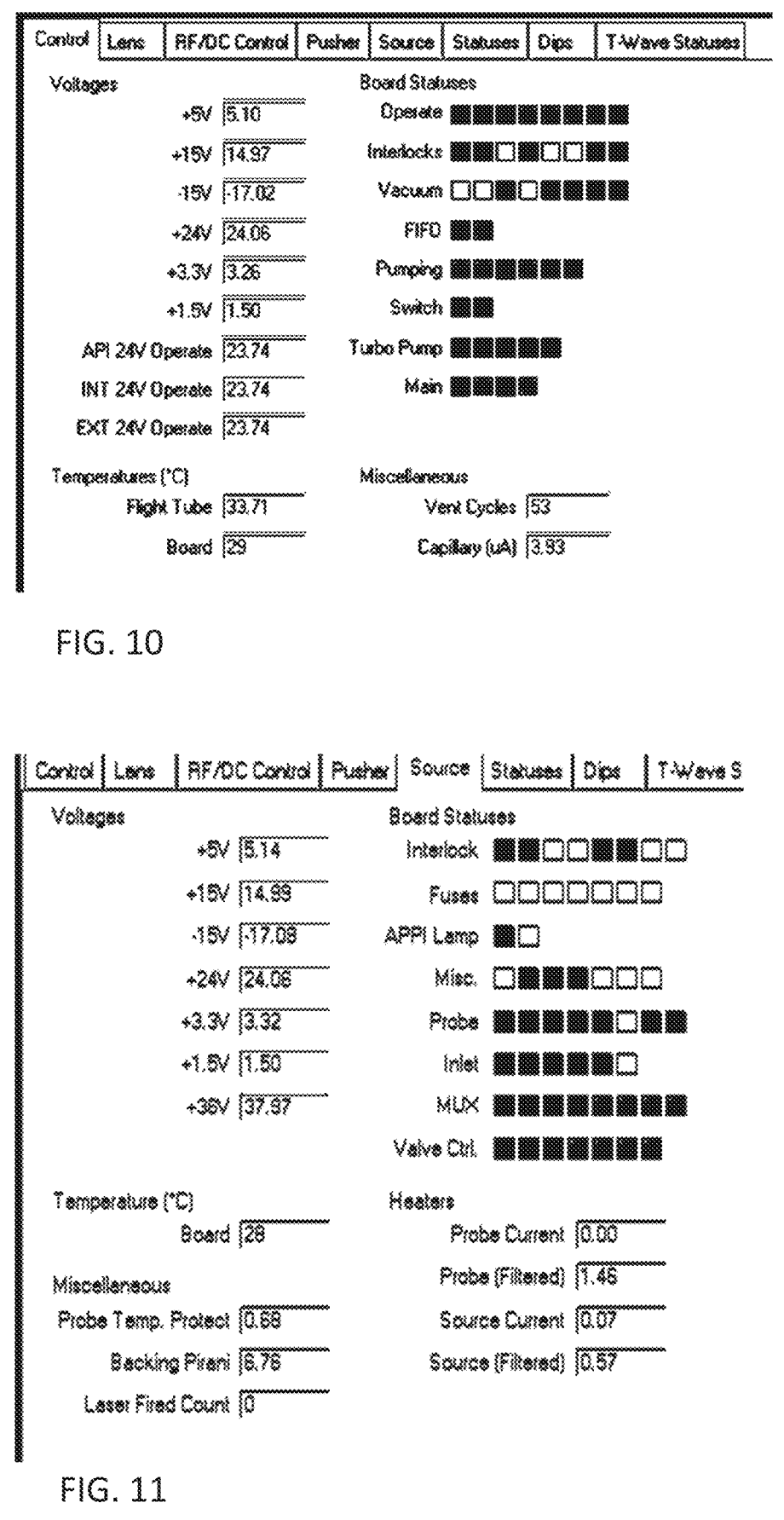

FIG. 10 shows for illustration purpose only, as one of possible examples, a representation of some of the operational parameters of the MS module 50 of FIG. 1 that can be monitored, like voltage values, current values and temperature values with respect to a main printed circuit board and different module components connected thereto.

FIG. 11, which is complementary to FIG. 10, shows some other operational parameters of the MS module 50 and, in particular, of the LC/MS interface 60 that can be monitored, like voltage values, current values and temperature related to the ionization source.

Figures 12, 13:
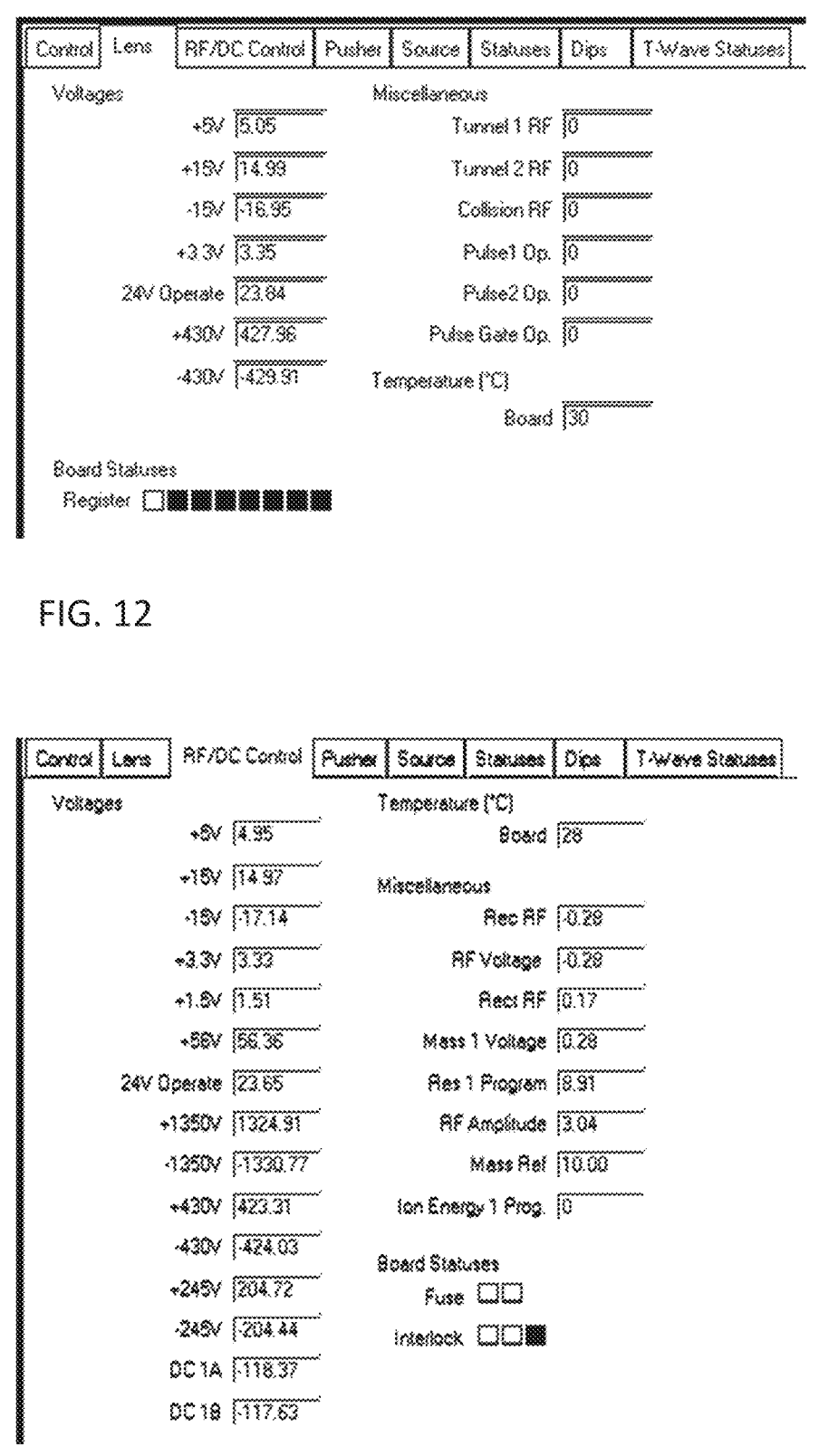

FIG. 12 and FIG. 13, which are complementary to FIGS. 10 and 11, show some other operational parameters of the MS module 50 that can be monitored, like voltage values and radio frequency values related to ion optics and quadrupole respectively.

Otherwise, the operational parameters from the MS module 50 may comprise raw data with respect to at least one of gas pressure, gas temperature, applied voltages and currents, flow rates, radio frequency. Although not shown in the figure, the one or more quality control and/or maintenance procedures may comprise any one or more of running a calibration procedure and/or a QC sample, checking ionization source clean status, re-tuning of MS module, re-initialization of the MS module, checking and eventually repairing or replacing a flow meter, checking and eventually repairing or replacing an ionization source heater, checking and eventually repairing or replacing a control board.

Although not shown, it can be possible to imagine similar examples for the sample preparation module 20 as well.

Figure 14:
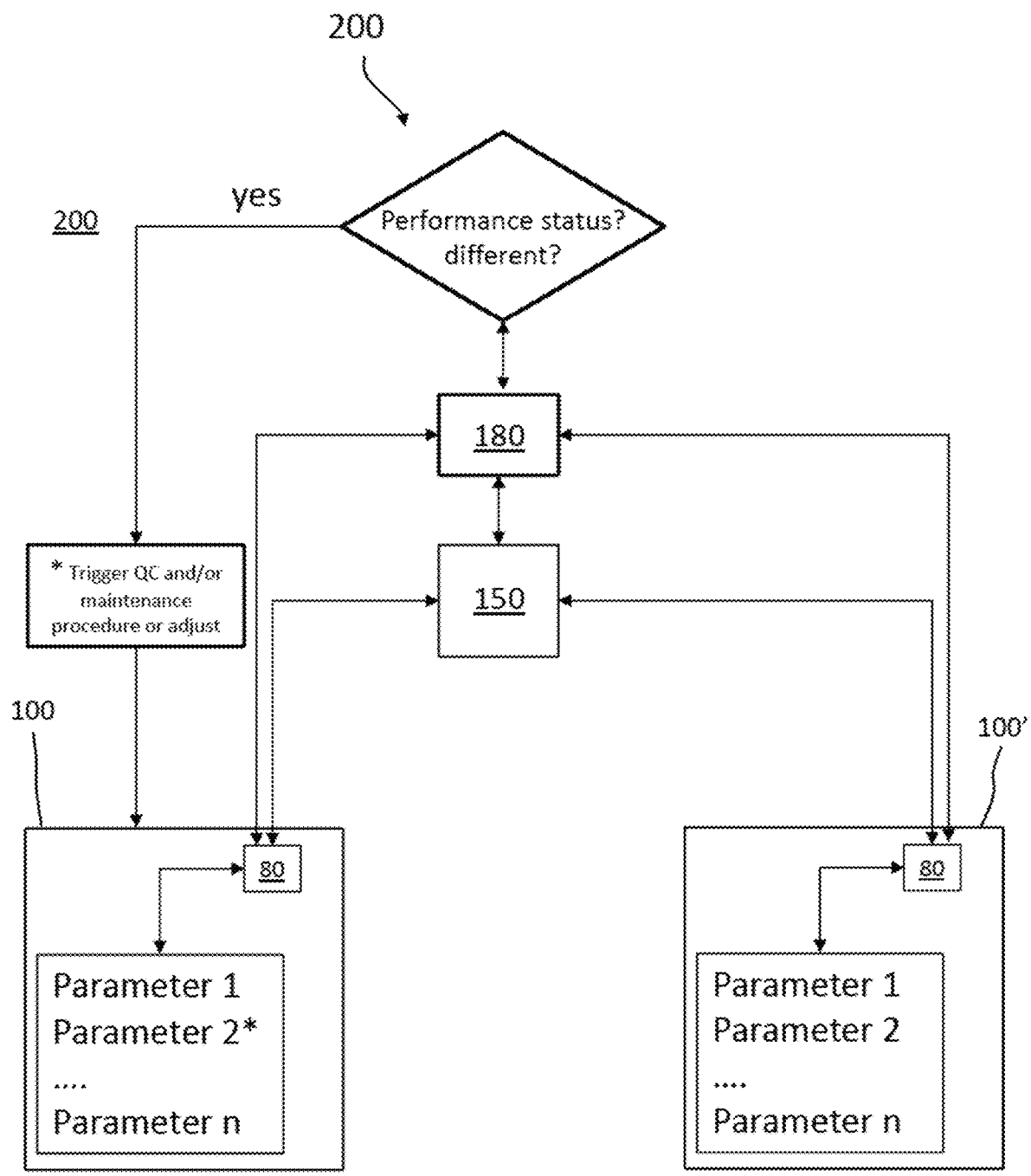
FIG. 14 illustrates schematically an example of interconnected laboratory system according to an embodiment of the present disclosure.

FIG. 14 schematically shows an example of interconnected laboratory system 200 comprising a plurality of clinical diagnostic systems 100, 100'.

The interconnected laboratory system 200 further can comprise a central data receiving device 150 and a central controller 180.

In particular, the central data receiving device 150 can be configured to receive data from the monitoring of the predetermined set of operational parameters from the plurality of clinical diagnostic systems.

The central controller 180 can be connected to the central data receiving device 150 and can be programmed to compare data from different clinical diagnostic systems 100, 100' and/or from one or more clinical diagnostic systems 100 with data from one or more reference clinical diagnostic systems 100'. The central controller 180 can be further programmed to trigger one or more of a quality control procedure and/or maintenance procedure, with respect to any of the clinical diagnostic systems 100 whenever its performance status deviates from the performance status of the other clinical diagnostic system 100' or systems it is compared to and/or to adjust one or more specification ranges for any of the operational parameters 1-$n$ of any one or more of the clinical diagnostic systems 100.

In addition, or in alternative, the central controller 180 in direct communication with the controllers 80 of the clinical diagnostic systems 100, 100' may be programmed to monitor any QC and/or maintenance procedures triggered by the controllers 80.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A clinical diagnostic system, the clinical diagnostic system comprising:
    a sample preparation module for the automated preparation of samples;
    a liquid chromatography (LC) separation module coupled to the sample preparation module via a sample preparation/LC interface;
    a mass spectrometer (MS) module coupled to the LC separation module via an LC/MS interface;
    a result calculation module for identifying and/or quantifying analytes or substances of interest contained in the samples and passed through the LC separation module and the MS module; and
    a controller programmed to monitor a predetermined set of operational parameters (1-$n$) indicative of a performance status of the clinical diagnostic system, trigger a quality control procedure and/or a maintenance procedure whenever one or more parameters (1-$n$) of the predetermined set of operational parameters (1-$n$) is out of specification, and minimize the quality control and/or maintenance procedures as long as the set of operational parameters (1-$n$) remains within specification.

2. The clinical diagnostic system according to claim 1, wherein the predetermined set of operational parameters (1-$n$) comprises a first subset based on data from the result calculation module and a second subset based on raw data from the sample preparation module, LC separation module, and MS module.

3. The clinical diagnostic system according to claim 2, wherein the controller, following a passed quality control procedure, is programmed to trigger one or more of a further quality control procedure and/or maintenance procedure whenever one or more parameters (1-$n$) of the first subset of operational parameters (1-$n$) is out of specification and to minimize further quality control and/or maintenance procedures as long as the first subset of operational parameters (1-$n$) remains within specification.

4. The clinical diagnostic system according to claim 3, wherein, whenever one or more parameters (1-$n$) of the first subset of operational parameters (1-$n$) is out of specification, the controller is programmed to check the raw data of the second subset of operational parameters (1-$n$) and to trigger one or more of a further quality control procedure and/or maintenance procedure whenever one or more parameters (1-$n$) of the second subset of operational parameters (1-$n$) is out of specification, and to minimize further quality and/or maintenance procedures as long as the second subset of operational parameters (1-$n$) remains within specification.

5. The clinical diagnostic system according to claim 2, wherein the first subset of operational parameters (1-$n$) comprises at least one of shape of LC and/or MS peaks, analyte elution/retention time, ratio of adjacent peak heights, signal/noise ratio, analyte signal intensity, background signal intensity, slope of background signal line, m/z value of peak maximum, m/z mass accuracy, calculated concentration of analyte, calculated concentration of QC substance.

6. The clinical diagnostic system according to claim 5, wherein the peaks are one or a plurality of any one or more of an analyte peak, an analyte fragment peak or isotope peak, a QC substance peak or reference substance peak added to a sample or to a reagent, or a fragment peak thereof or isotope peak thereof.

7. The clinical diagnostic system according to claim 5, wherein depending on the operational parameter or parameters (1-$n$) that are out of specification the one or more quality control and/or maintenance procedures comprise any one or more of running a calibration procedure and/or a QC sample, adjusting any one or more of LC conditions such as elution gradient, flow rate, pressure and temperature, changing eluents, regenerating or replacing an LC column, re-initialization of the MS module, tuning and calibration of the MS module, adjusting any one or more of the MS conditions such as adjusting of voltages, of gas pressure and temperature in ionization source, cleaning of any parts of the sample preparation module, LC module, MS module, checking and eventually replacing a QC sample.

8. The clinical diagnostic system according to claim 2, wherein the second subset of operational parameters (1-$n$) related to the sample preparation module comprises raw data with respect to at least one of power/energy consumption and/or voltage/amperage of electrically powered functional units, linear and/or rotational velocity and/or position of drive units and/or driven functional units, pressure in fluidic system.

9. The clinical diagnostic system according to claim 8, wherein depending on the operational parameter or parameters (1-$n$) that are out of specification, the one or more quality control and/or maintenance procedures comprise any one or more of running a calibration procedure and/or a QC sample, repairing or exchanging drive units and/or driven functional units or parts thereof, checking for leakage or loose connections and eventually replacing fittings or tightening, checking for clogging, for presence of foam or clot in samples or air in the fluidic system and eventually running an event specific protocol, checking for correct positioning of consumables or for sufficient test fluid volume and eventually exchanging or replacing consumables, checking alignment of drives and eventually re-adjusting alignment.

10. The clinical diagnostic system according to an claim 2, wherein the second subset of operational parameters (1-$n$) related to the LC separation module comprises raw data with respect to at least one of liquid pressure, gas pressure, temperature, flow rate, consumable level, waste level, power/energy consumption and/or voltage/amperage of electrically powered functional units, linear and/or rotational velocity and/or position of drive units and/or driven functional units.

11. The clinical diagnostic system according to claim 10, wherein depending on the operational parameter or parameters (1-$n$) that are out of specification, the one or more quality control and/or maintenance procedures comprise any one or more of running a calibration procedure and/or a QC sample, checking for leakage or loose connections and eventually replacing fittings or tightening, replacing or refilling eluents, regenerating or replacing an LC column, checking and eventually repairing or replacing a heater, checking and eventually repairing or replacing valves or pumps.

12. The clinical diagnostic system according to claim 2, wherein the second subset of operational parameters (1-$n$) related to the MS module comprises raw data with respect to at least one of gas pressure, gas temperature, applied voltages and currents, flow rates, radio frequency.

13. The clinical diagnostic system according to claim 12, wherein depending on the operational parameter or parameters (1-$n$) that are out of specification, the one or more quality control and/or maintenance procedures comprise any one or more of running a calibration procedure and/or a QC sample, checking ionization source clean status, re-tuning of MS module, re-initialization of the MS module, checking and eventually repairing or replacing a flow meter, checking and eventually repairing or replacing an ionization source heater, checking and eventually repairing or replacing a control board.

14. An interconnected laboratory system, the interconnected laboratory system comprising:
a plurality of clinical diagnostic systems according to claim 1;
a central data receiving device; and
a central controller, wherein the central data receiving device is configured to receive data from the monitoring of the predetermined set of operational parameters (1-$n$) from the plurality of clinical diagnostic systems and wherein the central controller is programmed to compare data from different clinical diagnostic systems and/or from one or more clinical diagnostic systems with data from one or more reference clinical diagnostic systems and trigger one or more of a quality control procedure and/or maintenance procedure, with respect to any of the clinical diagnostic systems whenever its performance status deviates from the performance status of the other clinical diagnostic system or systems it is compared to and/or adjust one or more specification ranges for any of the operational parameters (1-$n$) of any one or more of the clinical diagnostic systems.

15. A clinical diagnostic method, the clinical diagnostic method comprising:
monitoring a predetermined set of operational parameters (1-$n$) indicative of a performance status of a clinical diagnostic system according to claim 1;
triggering a quality control procedure and/or a maintenance procedure whenever one or more parameters (1-$n$) of the predetermined set of operational parameters (1-$n$) is out of specification; and
minimizing the quality control and/or maintenance procedures as long as the set of operational parameters (1-$n$) remains within specification.

* * * * *